United States Patent
Langley et al.

(10) Patent No.: US 11,097,057 B2
(45) Date of Patent: Aug. 24, 2021

(54) CANNULAS HAVING WALL STRENGTHENING FEATURES, AND RELATED SYSTEMS AND METHODS

(71) Applicant: Intuitive Surgical Operations, Inc., Sunnyvale, CA (US)

(72) Inventors: Douglas S. Langley, Milford, CT (US); Justin Krom, Southington, CT (US); Robert C. Reid, Fairfield, CT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 761 days.

(21) Appl. No.: 15/648,100

(22) Filed: Jul. 12, 2017

(65) Prior Publication Data

US 2018/0021517 A1 Jan. 25, 2018

Related U.S. Application Data

(60) Provisional application No. 62/365,807, filed on Jul. 22, 2016.

(51) Int. Cl.
*A61M 5/31* (2006.01)
*A61B 17/02* (2006.01)
(Continued)

(52) U.S. Cl.
CPC ....... *A61M 5/3134* (2013.01); *A61B 17/0218* (2013.01); *A61B 17/3421* (2013.01);
(Continued)

(58) Field of Classification Search
CPC . A61B 17/34; A61B 17/3421; A61B 17/3431; A61B 2017/3433;
(Continued)

(56) References Cited

U.S. PATENT DOCUMENTS 5,697,913 A 12/1997 Sierocuk et al.
6,325,790 B1 * 12/2001 Trotta .................. A61L 29/049
600/433

(Continued)

FOREIGN PATENT DOCUMENTS

WO WO-2015142812 A1 9/2015
WO WO-2015142814 A1 9/2015

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Amber R Stiles
*Assistant Examiner* — Alexandra Lalonde
(74) *Attorney, Agent, or Firm* — Jones Robb, PLLC

(57) ABSTRACT

A cannula may include a bowl portion comprising a first opening and a second opening, and an insertion tube extending from the bowl portion. The insertion tube defines a passage extending from the second opening and terminating in a distal end opening. The passage is configured to receive an instrument to be advanced through the cannula. The insertion tube has a transparent portion extending proximally from the distal end opening, and a strengthened portion extending proximally from the transparent portion.

20 Claims, 14 Drawing Sheets

(51) Int. Cl.
*A61M 25/00* (2006.01)
*A61B 17/34* (2006.01)
*A61B 17/00* (2006.01)

(52) U.S. Cl.
CPC ...... *A61M 25/005* (2013.01); *A61M 25/0021* (2013.01); *A61M 25/0026* (2013.01); *A61M 25/0052* (2013.01); *A61B 2017/00902* (2013.01); *A61M 2005/3118* (2013.01); *A61M 2025/0042* (2013.01)

(58) Field of Classification Search
CPC .... A61B 2017/3447; A61B 2017/3449; A61B 2017/345; A61B 2017/00902; A61B 17/3417; A61M 3/0279; A61M 25/005; A61M 25/0052; A61M 25/0053; A61M 5/3134; A61M 2025/0042; A61M 25/0054; A61M 25/0021
See application file for complete search history.

(56) References Cited

U.S. PATENT DOCUMENTS

| | | | |
|---|---|---|---|
| 7,316,699 B2 | 1/2008 | McFarlane | |
| 2005/0043682 A1* | 2/2005 | Kucklick | A61B 17/3421 604/164.09 |
| 2009/0234293 A1* | 9/2009 | Albrecht | A61B 17/3421 604/167.02 |
| 2011/0288532 A1* | 11/2011 | Faherty | A61M 25/0017 604/525 |
| 2011/0319839 A1* | 12/2011 | Del Vecchio | A61B 17/3468 604/272 |
| 2012/0232574 A1* | 9/2012 | Kim | A61F 2/2451 606/191 |
| 2013/0116510 A1* | 5/2013 | Lutze | A61B 1/32 600/208 |
| 2013/0325031 A1 | 12/2013 | Schena et al. | |
| 2013/0325033 A1 | 12/2013 | Schena et al. | |
| 2014/0194895 A1* | 7/2014 | Crews | A61B 17/3421 606/130 |
| 2014/0207084 A1* | 7/2014 | Webb | A61B 17/3462 604/264 |
| 2015/0123355 A1 | 5/2015 | Castro et al. | |

* cited by examiner

CANNULAS HAVING WALL STRENGTHENING FEATURES, AND RELATED SYSTEMS AND METHODS

CROSS-REFERENCE TO RELATED APPLICATIONS

This application claims priority to U.S. Provisional Application No. 62/365,807 filed Jul. 22, 2016, the contents of which are incorporated herein in their entirety.

TECHNICAL FIELD

The present disclosure relates generally to cannulas used in minimally-invasive surgery and other medical procedures, and related systems and methods. More specifically, the present disclosure relates to a cannula having a cannula insertion tube that provides transparency and strengthening features.

INTRODUCTION

Remotely controlled surgical instruments, including surgical instruments operated at least in part with computer assistance, such as instruments operated with robotic "master-slave" and other remote telepresence technology, are often used in minimally invasive medical procedures. In such teleoperated, computer-assisted surgical systems, surgeons manipulate input devices at a surgeon console, and those "master" inputs are passed to a patient side cart that interfaces with one or more remotely controlled surgical instruments coupled to the patient side cart. Based on the surgeon inputs at the surgeon console, the one or more remotely controlled surgical instruments are actuated at the patient side cart to operate on the patient, thereby creating a master-slave control relationship between the surgeon console and the surgical instrument(s) at the patient side cart.

Various minimally invasive procedures, whether performed manually or via robotic, computer-assisted systems, utilize cannulas that are inserted through a port, incision, or opening in a body wall (e.g., a patient's body wall). Surgical instruments are then introduced through the cannula to provide access to a remote surgical or treatment (including diagnostic) site within the body. In some cases, cannulas are made of relatively inexpensive materials, such as, for example, plastic, so that they may be disposed of after a single use.

To reduce trauma to the body wall through which a cannula is inserted, it is desirable to minimize the outer lateral dimensions (e.g., diameter) of the cannula so that the size of the port, incision, or opening in the body wall may be minimized. To provide stability and reduce trauma to the body wall though which a cannula is inserted, it is desirable that the shape of the cannula remains relatively fixed once inserted, and that bending and kinking of the cannula are minimized. Moreover, in procedures relying on insufflation gas pressure above ambient pressure, cannulas generally include sealing elements to seal against the instruments being inserted through the inlet opening of the cannula, and also to seal against the body wall around an outer lateral surface of the cannula.

In some manual laparoscopic surgical procedures, and in robotic, computer-assisted surgery in which the remote center of motion of movement of surgical instruments is generally stationary in space, the cannula generally stays in place with reference to the body wall of the patient in order to maintain stability during the procedure and also a seal with the body wall. Advances in computer-assisted surgery have increased the ability to change the location of the remote center of motion in space during a surgical procedure. However, this may lead to an increase in the torque and other forces acting about the remote center of a cannula (i.e., bending forces). For example, the use of table motion and/or the use of a software-defined remote center of motion manipulation arm holding a cannula, may result in a change of the location of the remote center of motion in space, which may cause increased torque and other forces on the cannula. In view of the relatively fixed position of the cannula, such forces have the potential to bend, kink, and/or otherwise deform the cannula.

Certain body walls impart relatively higher forces upon inserted cannulas. For example, body walls in thoracic regions wherein cannulas are generally inserted between rib bones during surgery or treatment can impart relatively higher bending forces on a cannula. Also, body walls that are relatively more muscular and/or relatively thicker can impart relatively higher bending forces on a cannula. Moreover, instruments inserted through the cannula during a procedure also may subject the cannula to forces tending to bend and/or kink the cannula in undesirable ways, in particular as the instruments take on differing curvatures along their lengths as they navigate to a remote site.

Accordingly, it may be desirable to provide a plastic cannula with improved resistance to bending forces, such as forces that generate relatively high torque about the remote center of the cannula. Moreover, it may be desirable to provide cannulas with transparency and/or relatively small outer dimensions, while maintaining desirable strength, in particular strength at areas of the cannula subject to potentially high forces.

SUMMARY

Exemplary embodiments of the present disclosure may solve one or more of the above-mentioned problems and/or may demonstrate one or more of the above-mentioned desirable features. Other features and/or advantages may become apparent from the description that follows.

A cannula in accordance with various exemplary embodiments of the present disclosure has a bowl portion comprising a first opening and a second opening, the first opening being larger than the second opening. The cannula further has an insertion tube extending from the bowl portion and defining a passage that extends from the second opening of the bowl portion and terminates in a distal end opening. The passage may be configured to receive an instrument to be advanced through the cannula. The insertion tube has a transparent portion extending proximally from the distal end opening, and a strengthened portion extending proximally from the transparent portion.

In accordance with another aspect of the present disclosure, a method of making a cannula that has an insertion tube configured for advancement of surgical instruments therethrough is disclosed. The method can include making a first portion of a length of the insertion tube from a transparent plastic material, and making a second portion of the length of the insertion tube from a material having a higher strength than the transparent plastic material.

In accordance with yet another exemplary embodiment of the present disclosure, a method of using a cannula can include inserting at least a portion of the insertion tube through a body wall, the portion having a transparent tube wall. The method can further include positioning the insertion tube such that the transparent tube wall is at a location of the body wall and such that a portion of the insertion tube having a higher strength than the portion having the transparent side wall extends away from the body wall relative to a direction of the inserting.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

Figure 1:
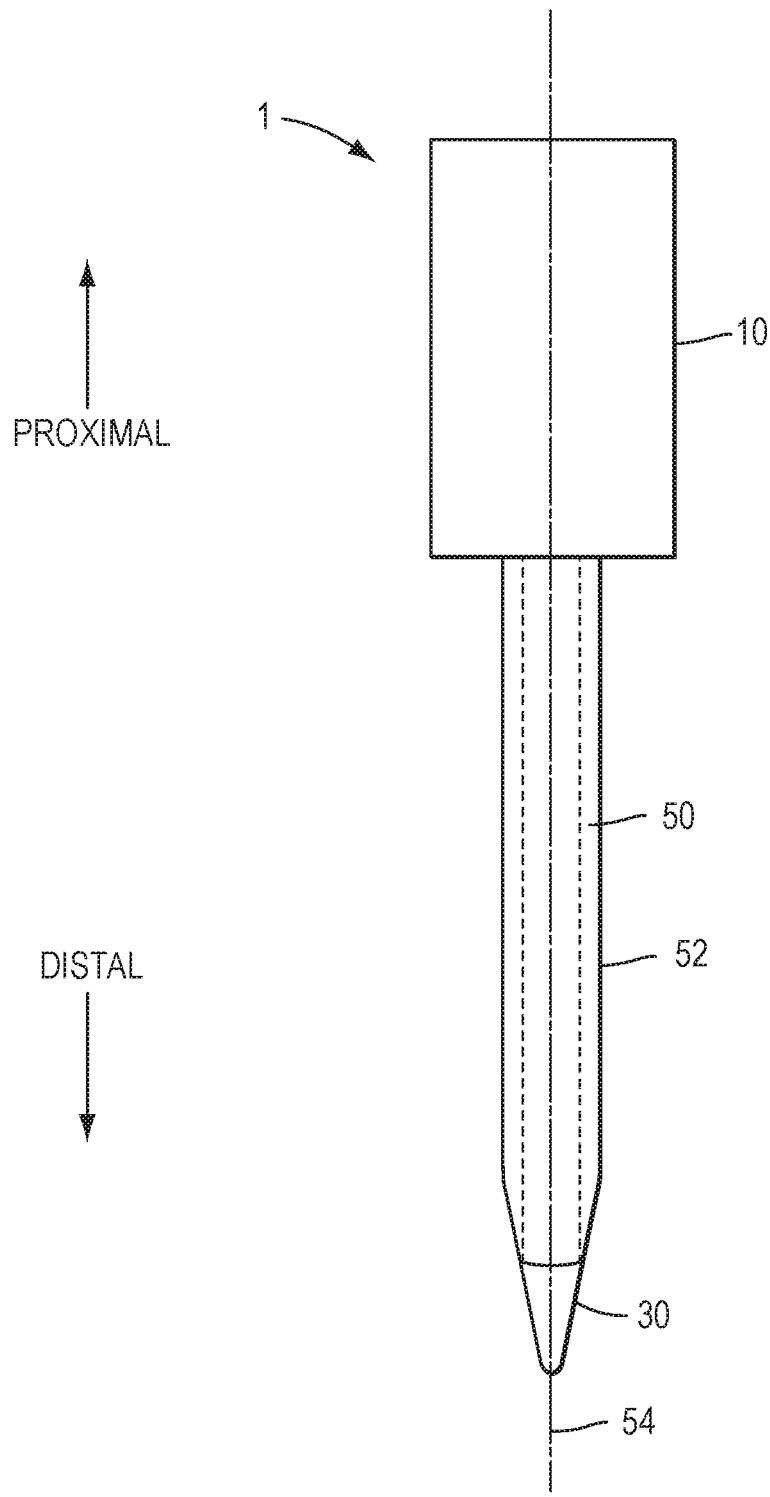
FIG. 1 is a side schematic view of a surgical instrument apparatus.

Although the following detailed description makes reference to exemplary illustrative embodiments, many alternatives, modifications, and variations thereof will be apparent to those skilled in the art and are contemplated as within the scope of the present disclosure and claims. Accordingly, it is intended that the claimed subject matter is provided its full breadth of scope and to encompass equivalents.

DESCRIPTION OF EXEMPLARY EMBODIMENTS

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

This description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. In the orientation of the figures in the application, relative proximal and distal directions of the devices have been labeled.

The present disclosure contemplates cannulas, and related systems and methods, with one or more wall strengthening features. Cannulas in accordance with various exemplary embodiments of the present disclosure are designed based in part on, for example, a variety of parameters that can be varied to achieve enhanced strength and resistance to bending forces of a cannula, while also allowing design flexibility to meet a range of applications.

In at least some cannula applications, transparency is desired, particularly in the sections around and distal from the remote center of the cannula, so that when an endoscopic device is inserted through the cannula, the endoscopic device can be pulled back at least partially into the cannula thereby providing a wider field of view of the surgical or treatment site. Additionally, transparency at this portion of a cannula allows a surgeon to check that the remote center of the cannula is properly disposed within an opening, such as a port, incision, or the like in the body wall of a patient or other access opening to a remote site. The present disclosure therefore contemplates cannulas having at least a portion with transparency sufficient to permit surveillance of instruments being advanced and withdrawn through the cannula as well as observation of the disposition of the cannula itself relative to the body wall.

Although, cannula strength and resistance to bending forces can be enhanced by increasing the lateral (e.g., radial) thickness of the walls of the cannula, increasing the thickness, at least at and around the remote center of a cannula, requires that the port, incision, or opening in the body wall be made bigger, which induces more trauma to the body wall as a result. The present disclosure therefore contemplates cannulas having relatively high strength while maintaining relatively thin-walled structures, in particular along the insertion tube portion of the cannula that is introduced through a body wall.

In instances where a plastic material is used to make the cannula, for example, to provide disposability and/or transparency, a cannula also may be strengthened by adding filler(s), such as glass fibers and/or carbon graphite fibers, to the blend of material that the cannula is made from (i.e., compounding) so as to increase the strength of the plastic cannula without changing its dimensions. However, fillers such as glass increase the opacity of an otherwise transparent plastic material such that the optical advantages of having a transparent cannula, as described above, are lost. The present disclosure thus contemplates providing a relatively high strength cannula having transparency sufficient to permit observation of instruments being advanced, maintained, and withdrawn through the cannula.

In at least some cannula applications, cannulas may be configured such that the inner diameter of the cannula tapers from the proximal end of the cannula to the distal end of the cannula thereby providing both a distal tip of the cannula that engages or otherwise supports the shaft of the instrument inserted therethrough and clearance along portions proximal from the distal tip that allow for the instrument shaft to bend under side loads at the end effector without undesirably interacting with the cannula. However, under large enough side loads, the clearance between the instrument shaft and the tapered inner side wall of the cannula can be exhausted and result in binding and/or kinking, or other deformation of the cannula, that stops the instrument from being inserted into or withdrawn from the cannula and potentially damages the cannula. The present disclosure thus additionally contemplates providing cannulas with enough strength to resist deformation as result of consumption of the clearance between the instrument shaft and the inner side wall (e.g., tapered side wall) of the cannula.

In accordance with the present disclosure, the structural and compositional configurations of the cannulas disclosed herein provide cannulas with strengthening features that are resilient against and/or resistant to bending forces that may impart torque about a remote center or another portion of the cannula, such as, for example, forces applied by a body wall in an inserted position of the cannula through the body wall and/or associated with inserted instruments interacting with portions of the cannula. Further, structural and compositional configurations of the cannulas disclosed herein provide relatively high strength cannulas that have desirable transparency, minimized lateral dimensions (e.g., diameter), and/or are made from relatively inexpensive materials (e.g., plastics) and manufacturing techniques, thereby permitting disposability.

To enhance the resistance of a cannula to deformation (e.g., bending and/or kinking) forces (e.g., enhanced stiffness) while also maintaining desirable transparency, various exemplary embodiments of cannulas include a strengthened portion along a length of the cannula insertion tube and a transparent portion along a length of the cannula insertion tube. For the purposes of the present disclosure, a "strengthened portion" is defined as a portion that exhibits relatively higher stiffness, resistance to bending moments, and/or resistance to shear forces, compared to at least another portion of the cannula. Also, for the purposes of the present disclosure, a "transparent portion" is defined as a portion that has relatively higher transparency compared to at least another portion of the cannula. In various exemplary embodiments, the transparent portion and the strengthened portion are differing portions of the cannula.

A strengthened portion may be made from a plastic compounded with glass and/or carbon fibers, and a transparent portion made from a more transparent plastic material. Although a strengthened portion and a transparent portion may each be provided in various locations along the cannula, in one exemplary embodiment a strengthened portion may be proximal from a remote center of a cannula and a transparent portion may be distal from the strengthened portion. In various exemplary embodiments the transparent portion may extend from a portion proximal from the remote center of the cannula to a distal end of the cannula. According to at least some exemplary embodiments, a strengthened portion and a transparent portion may be joined by, for example, welding, overmolding, two-shot molding, or solvent bonding.

To further enhance the stiffness of a cannula, additional various exemplary embodiments of cannulas include a variation in the wall thickness of the cannula along its length. For example, in cannulas having a cannula insertion tube with a constant or slightly distally tapered inner diameter defining the cannula insertion tube lumen, the cannula insertion tube may include a tapered outer surface region relative to other portions along a length of the cannula insertion tube. Such a tapered region may be configured such that the portion(s) of the tapered region with the greatest outer dimension (i.e., greatest lateral wall thickness) are located at one or more portions along the length of the cannula insertion tube that tend to be subject to relatively higher bending moments, and the portion(s) of the tapered region with the smallest outer dimensions (i.e., smallest lateral wall thickness) are located at a portion along the length of the cannula insertion tube where a body wall of a patient is intended to sit when the cannula is in an inserted position. In this way, the strength of the cannula may increase while minimizing the lateral dimensions of the cannula so as to not require a larger size port, opening, and/or incision within the body wall of a patient. Portion(s) of the tapered region with the smallest outer dimensions (i.e., smallest lateral wall thickness) could alternatively, or in addition to, be provided proximate to the body wall contact region of the cannula. A variable wall thickness that results in a tapered outer surface profile region can also provide increased retention forces by inhibiting the body wall from moving past a maximum lateral dimension end of the tapered region in response to a force tending to move the cannula in the axial direction relative to the body wall.

Transparent portions of cannulas in accordance with the present disclosure can be made of a relatively clear plastic material, for example, polycarbonate, acrylic, polysulfone (e.g., commercially available under the trademark Udel®) and/or any other suitable materials. Strengthened portions of cannulas in accordance with the present disclosure can be a plastic material compounded with glass, carbon, and/or aramid fibers, for example, polycarbonate, acrylonitrile butadiene styrene (ABS), polycarbonate-ABS, polypropylene, nylon, polyphenylsulfone (e.g., commercially available under the trademark Rodel®) and/or any other suitable materials. Those of ordinary skill in the art would understand, for example, that the material used for a cannula may be chosen based at least in part on intended application, strength/weight considerations, cost, overhead surgical space, incision size, and/or other design factors. For example, a cannula that is intended to be disposable may have a transparent portion made of polycarbonate and/or acrylic, and a strengthened portion made of fiber compounded polycarbonate, ABS, polycarbonate-ABS, polypropylene, and/or nylon. Further, an exemplary cannula that is intended to be reusable and/or autoclavable may have a transparent portion made of polysulfone (e.g., commercially available under the trademark Udel®) and/or an equivalent, and a strengthened portion made of fiber compounded polyphenylsulfone polymer (e.g., commercially available under the trademark Rodel®) and/or an equivalent.

Various exemplary embodiments of cannulas in accordance with the present disclosure also utilize rib features on at least a portion of the outer surface of the cannula tube. When such ribs are employed, the ribs may be configured to provide the tapered profiles of the cannula.

Figure 2A:
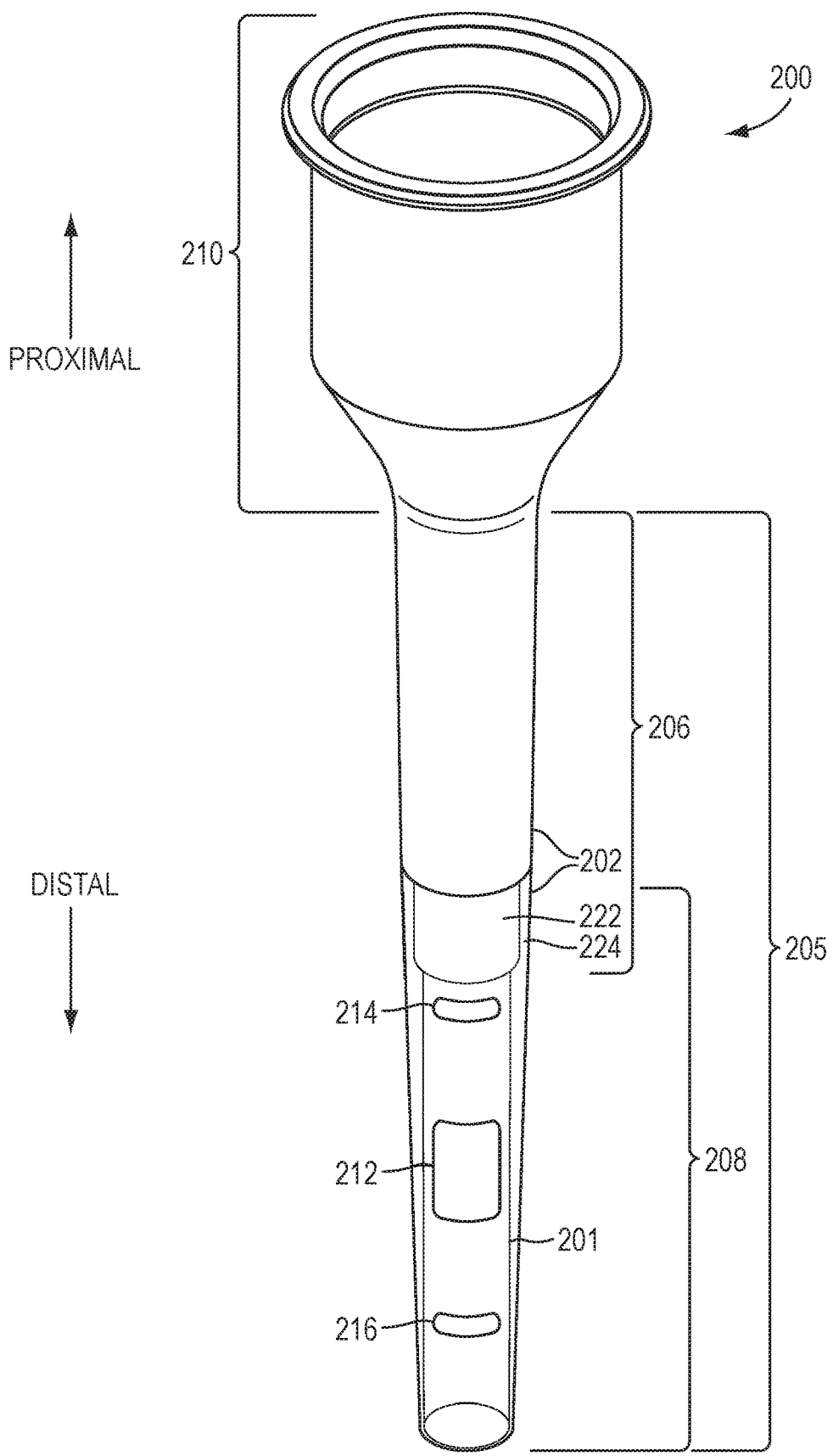
FIG. 2A is a perspective view of an exemplary embodiment of a cannula in accordance with the present disclosure.

FIG. 1 illustrates schematically an exemplary embodiment of a surgical instrument apparatus 1 that can be used in various laparoscopic or minimally invasive surgical procedures. A surgical instrument 30 having a force transmission actuation housing 10 at its proximal end is inserted through a cannula 50. In various exemplary embodiments, although not shown in FIG. 1, cannula 50 may have a proximal bowl (e.g., bowl portion 210 at FIG. 2A) that initially receives the surgical instrument shaft. In various embodiments, the bowl portion houses an elastomeric seal that allows for delivery and maintenance of insufflation gas pressure, and guides a surgical instrument being inserted through the cannula. Additionally, although not shown, a mounting boss configured to enable mounting of the cannula to a portion of a patient side cart of a teleoperated, robotic surgical system or otherwise may protrude from the bowl. Cannulas free of a bowl portion are also contemplated.

In some conventional configurations, cannula 50 has a substantially tubular (e.g., cylindrical or having an elongated rounded cross-section) outer lateral wall surface 52 that extends longitudinally and parallel to the longitudinal axis 54 of the cannula 50 such that the outer diameter of the cannula 50 is substantially uniform along its entire length. Being tubular, cannula 50 also has an inner lateral wall surface, hidden from view in FIG. 1. The inner lateral wall surface is substantially cylindrical, or of other cross-sectional shape, and substantially longitudinally parallel to the axial direction of the cannula 50. For example, the inner diameter and/or other lateral dimension of the cannula 50 can be substantially uniform along its entire length. Alternatively, the outer lateral wall surface 52 and/or the inner lateral wall surface may be slightly tapered to provide a generally frustoconical shape to the cannula, in particular to enable manufacture by molding techniques and instrument bending clearance, as described above. A thickness of the wall of the cannula having lateral inner and outer wall surfaces may be relatively small as compared to the inner hollow lumen (represented by thin dashed line) surrounded by the lateral inner wall surface.

Figure 5:
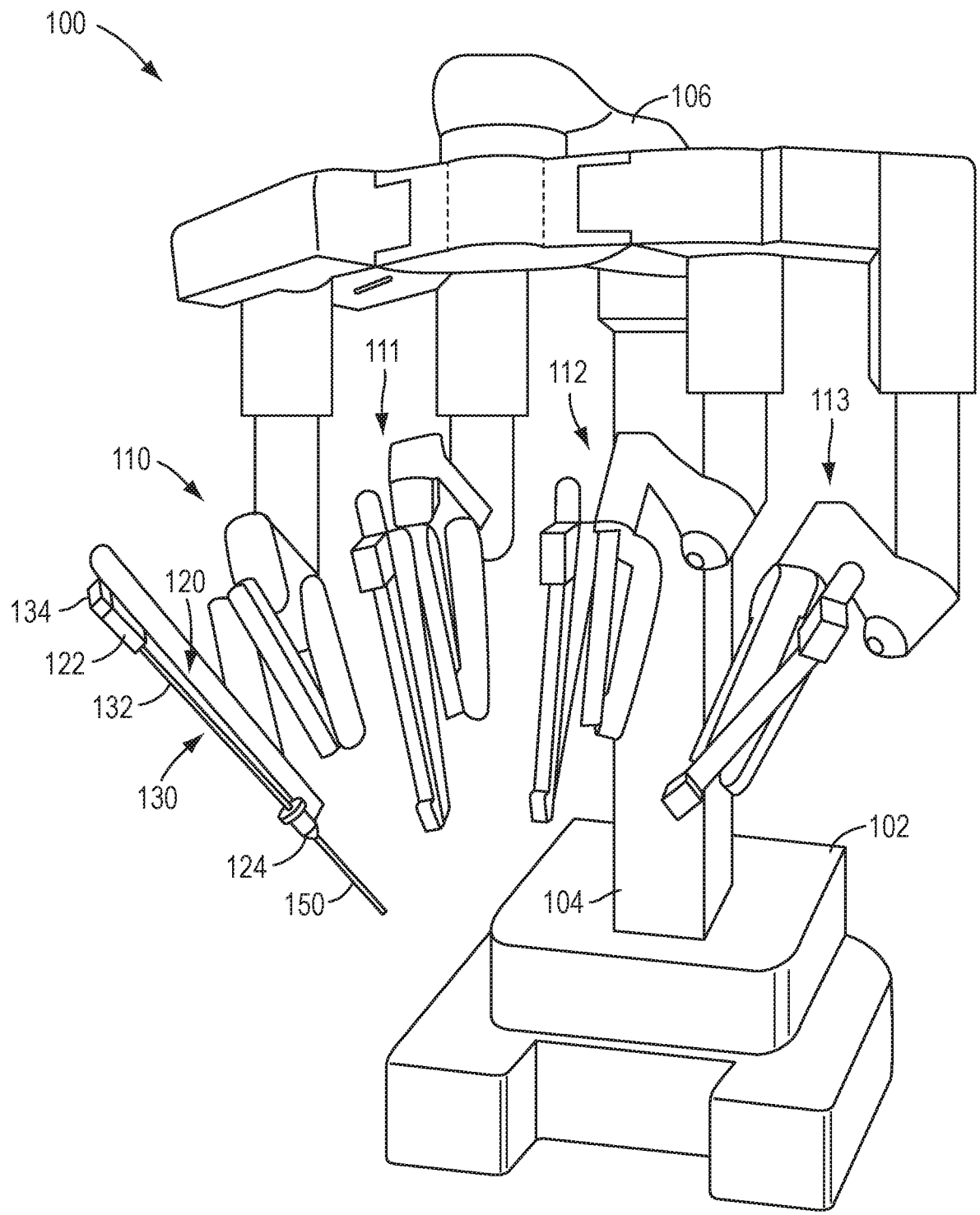
FIG. 5 is a perspective diagrammatic view of a patient side cart in accordance with an exemplary embodiment.

As discussed above, in accordance with various exemplary embodiments, cannulas and surgical instruments of the present disclosure are configured for use in teleoperated, computer-assisted surgical systems. Referring now to FIG. 5, an exemplary embodiment of a patient side cart 100 of a teleoperated, computer-assisted surgical system, to which cannulas and surgical instruments are configured to be mounted for use, is shown. Such a surgical system may further include a surgeon console (not shown) for receiving input from a user to control instruments of patient side cart 100, as well as an auxiliary control/vision cart (not shown), as described in, for example, U.S. Pub. No. US 2013/0325033, entitled "Multi-Port Surgical Robotic System Architecture" and published on Dec. 5, 2013, and U.S. Pub. No. US 2013/0325031, entitled "Redundant Axis and Degree of Freedom for Hardware-Constrained Remote Center Robotic Manipulator" and published on Dec. 5, 2013, each of which is hereby incorporated by reference in its entirety. Non-limiting, exemplary embodiments of teleoperated, computer-assisted surgical systems with which the principles of the present disclosure may be utilized include the da Vinci® Si (model no. IS3000) da Vinci® Si Surgical System, Single Site da Vinci® Surgical System, or a da Vinci® Xi Surgical System, available from Intuitive Surgical, Inc. of Sunnyvale, Calif.

Patient side cart 100, shown in FIG. 5, includes a base 102, a main column 104, and a main boom 106 connected to main column 104. Patient side cart 100 also includes a plurality of arms 110, 111, 112, 113, which are each connected to main boom 106. Arms 110, 111, 112, 113 each include an instrument mount portion 120 to which an instrument 130 may be mounted, which is illustrated as being attached to arm 110. Portions of arms 110, 111, 112, 113 may be manipulated during a surgical procedure according to commands provided by a user at the surgeon console. In an exemplary embodiment, signal(s) or input(s) transmitted from a surgeon console are transmitted to the control/vision cart, which may interpret the input(s) and generate command(s) or output(s) to be transmitted to the patient side cart 100 to cause manipulation of an instrument 130 (only one such instrument being mounted in FIG. 1) and/or portions of arm 110 to which the instrument 130 is coupled at the patient side cart 100.

Instrument mount portion 120 comprises an actuation interface assembly 122 and a cannula mount 124, with a force transmission mechanism 134 of instrument connecting with the actuation interface assembly 122, according to an exemplary embodiment. Cannula mount 124 is configured to hold a cannula 150 through which shaft 132 of instrument 130 may extend to a surgery site during a surgical procedure. Actuation interface assembly 122 contains a variety of drive and other mechanisms that are controlled to respond to input commands at the surgeon console and transmit forces to the force transmission mechanism 134 to actuate instrument 130, as those skilled in the art are familiar with.

Although the exemplary embodiment of FIG. 5 shows an instrument 130 and cannula 150 attached to only arm 110 for ease of viewing, an instrument and cannula may be attached to any and each of arms 110, 111, 112, 113. An instrument 130 may be a surgical instrument with an end effector or may be an endoscopic imaging instrument or other sensing instrument utilized during a surgical procedure to provide information, (e.g., visualization, electrophysiological activity, pressure, fluid flow, and/or other sensed data) of a remote surgical site. A surgical instrument with an end effector or an imaging instrument may be attached to and used with any of arms 110, 111, 112, 113. However, the embodiments described herein are not limited to the exemplary embodiment of FIG. 5 and various other teleoperated, computer-assisted surgical system configurations may be used with the exemplary embodiments described herein.

It is contemplated that the present disclosure can be applied to various cannula configurations, including, but not limited to, for example, cannula configurations disclosed in International Application Pub. No. WO 2015/142812 A1, entitled "SURGICAL CANNULAS AND RELATED SYSTEMS AND METHODS OF IDENTIFYING SURGICAL CANNULAS" and published Sep. 24, 2015, and International Application Pub. No. WO 2015/142814 A1, entitled "SURGICAL CANNULA MOUNTS AND RELATED SYSTEMS AND METHODS" and published Sep. 24, 2015, each of which is hereby incorporated by reference in its entirety.

With reference now to FIGS. 2A through 2E, an exemplary embodiment of cannula 200 in accordance with the present disclosure is illustrated. Cannula 200 includes a cannula insertion tube 205 that has strengthened portion 206 and a transparent portion 208. The cannula 200 further includes a bowl portion 210 at a proximal end thereof and from which the cannula insertion tube 205 extends. Bowl portion 210 can have a relatively wide opening at a proximal end of the cannula and may taper to a relative narrowed opening from which the insertion tube 205 extends. In various exemplary embodiments, bowl portion 210 has a funnel configuration with the cannula insertion tube 205 extending from a narrowed end of the funnel shaped bowl portion 210. In various exemplary embodiments, the strengthened portion 206 may be made of a reinforced plastic material. For example, the strengthened portion 206 may be made of a plastic compounded with strengthening fibers, such as, for example, glass, carbon, and/or aramid fibers, as described above. The strengthening fibers provide increased strength, but may decrease the transparency of the plastic material alone such that the strengthened portion 206 is relatively opaque. In one exemplary embodiment, the material of the strengthened portion is polycarbonate compounded with about 10% to about 30% fibers. The fibers may be at least one of glass fibers, carbon fibers, aramid fibers, and/or any other suitable fiber material. Alternatively, in an exemplary embodiment, the strengthened portion is made out of metal, such as, for example, stainless steel and/or any other suitable metal. The transparent portion 208 of the cannula insertion tube 205 may be made of a relatively transparent material, such as for example a clear plastic material as described above. In various exemplary embodiments, the transparent portion is made of polycarbonate and does not include reinforcement material, such as, strengthening fibers. When an endoscopic sensing device (e.g., an endoscopic image capture device) is inserted through a cannula 200 that has a cannula insertion tube 205, the relative transparency of the transparent portion 208 can provide a wider field of view of the surgical or treatment site as the endoscopic device is retracted at least partially into the distal end of the cannula 200 so that the endoscopic sensing device's distal end is disposed within the transparent portion 208.

Cannula insertion tube 205 has an inner lateral wall surface 201 (shown within the transparent portion 208 in FIGS. 2B and 2D, but hidden from view within the relatively opaque strengthened portion 206) and an outer lateral wall surface 202. The inner lateral wall surface 201 may be cylindrical or slightly distally tapered along the length, as described above. Also, the outer lateral wall surface 202 may be cylindrical or slightly distally tapered along the length, as described above. It is also contemplated that the outer lateral wall surface 202 can include two or more tapered portions along the length of its cannula insertion tube 205, in a fashion similar to outer lateral wall surface 302 of exemplary cannula 300, as shown and described below.

In various exemplary embodiments, the present disclosure contemplates providing the cannula with indicia that assists placement of the cannula relative to the body wall of a patient in an inserted position of the cannula. By way of non-limiting example, with reference again to FIGS. 2B and 2D, a portion of the outer lateral wall surface 202 includes a central body wall target 212. The outer lateral wall surface 202 also can include an upper body wall target 214 located proximal from the central body wall target 212 and a lower body wall target 216 located distal from the central body wall target 212. The body wall targets 212, 214, 216 provide guidance as to where the body wall should sit along the length of the cannula 200 when the cannula is inserted within the body wall of a patient. For example, it may be desirable for the body wall to be located at a region between the upper body wall target 214 and the lower body wall target 216 of the cannula 200. It may be further desirable for the body wall of a patient to be located at the central body wall target 212 of the cannula 200. The remote center 218 of the cannula 200 is located at or near the center of the central body wall target 212. Alternatively, it is also contemplated that the center of the central body wall target of a cannula can be offset from the remote center of the cannula.

Figure 2B:
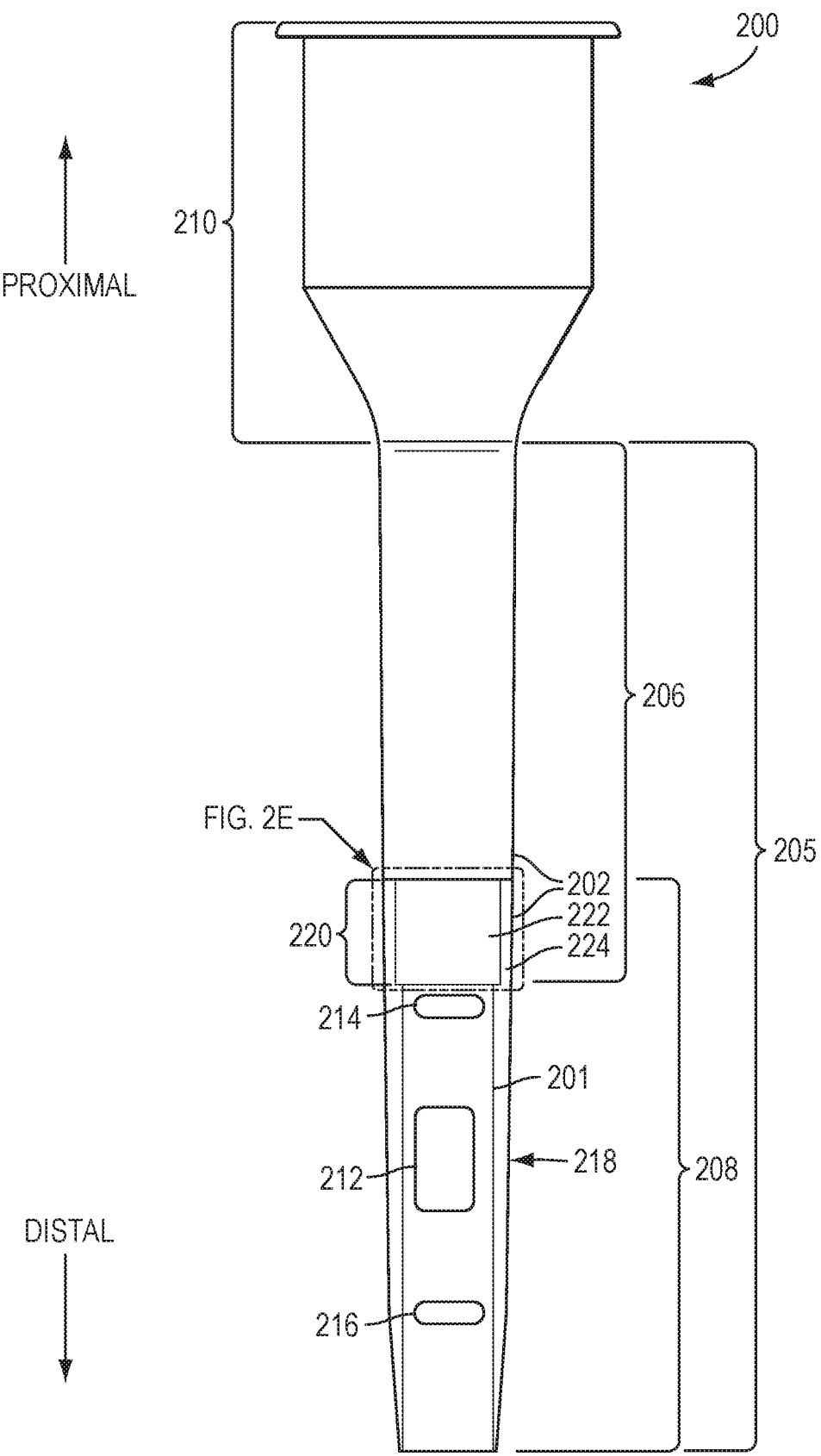
FIG. 2B is a side view of the cannula of FIG. 2A.
Figure 2C:
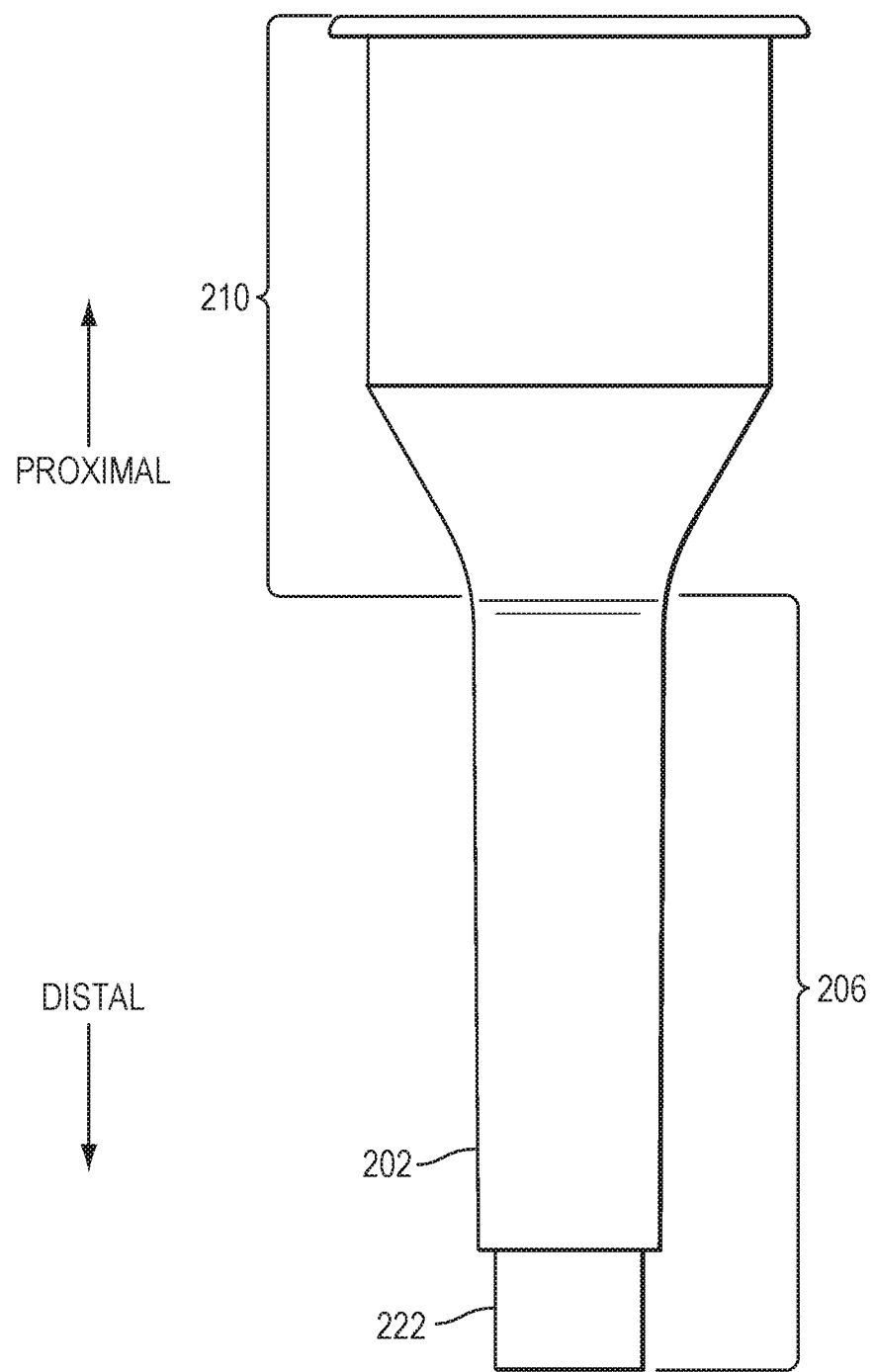
FIG. 2C is a detailed side view of the portions of the cannula of FIGS. 2A and 2B.
Figure 2D:
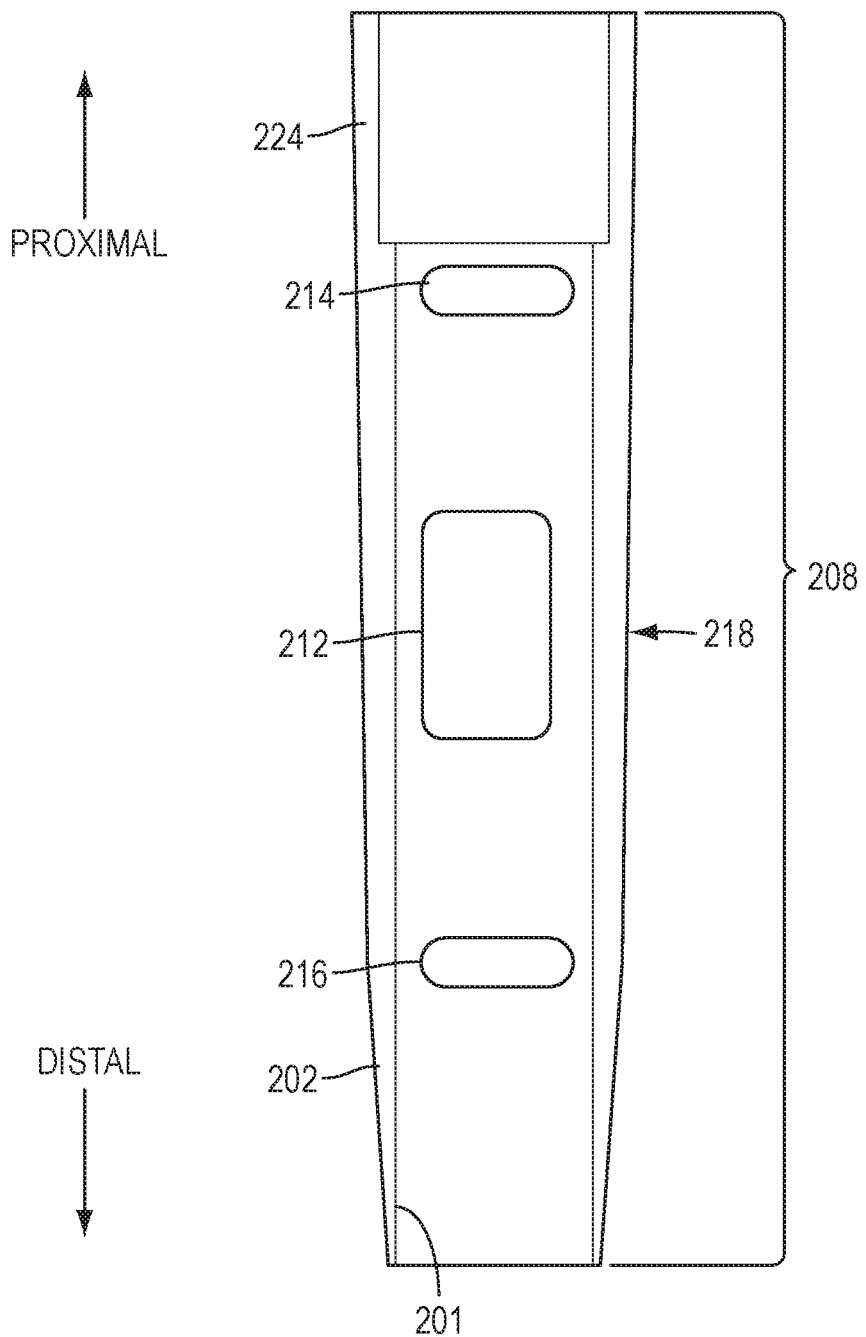
FIG. 2D is a detailed side view of another portion of the cannula of FIGS. 2A and 2B.

As shown in FIGS. 2B and 2D, the body wall targets 212, 214, 216 are disposed on the portion of the outer lateral wall surface 202 within the transparent portion 208 of the cannula 200. Alternatively, it is also contemplated that one or more of the body wall targets are disposed on the portion of the outer lateral wall surface within the strengthened portion 206. For example, the upper body wall target 214 could alternatively be disposed on the portion of the outer lateral wall surface within the strengthened portion 206.

Figure 2E:
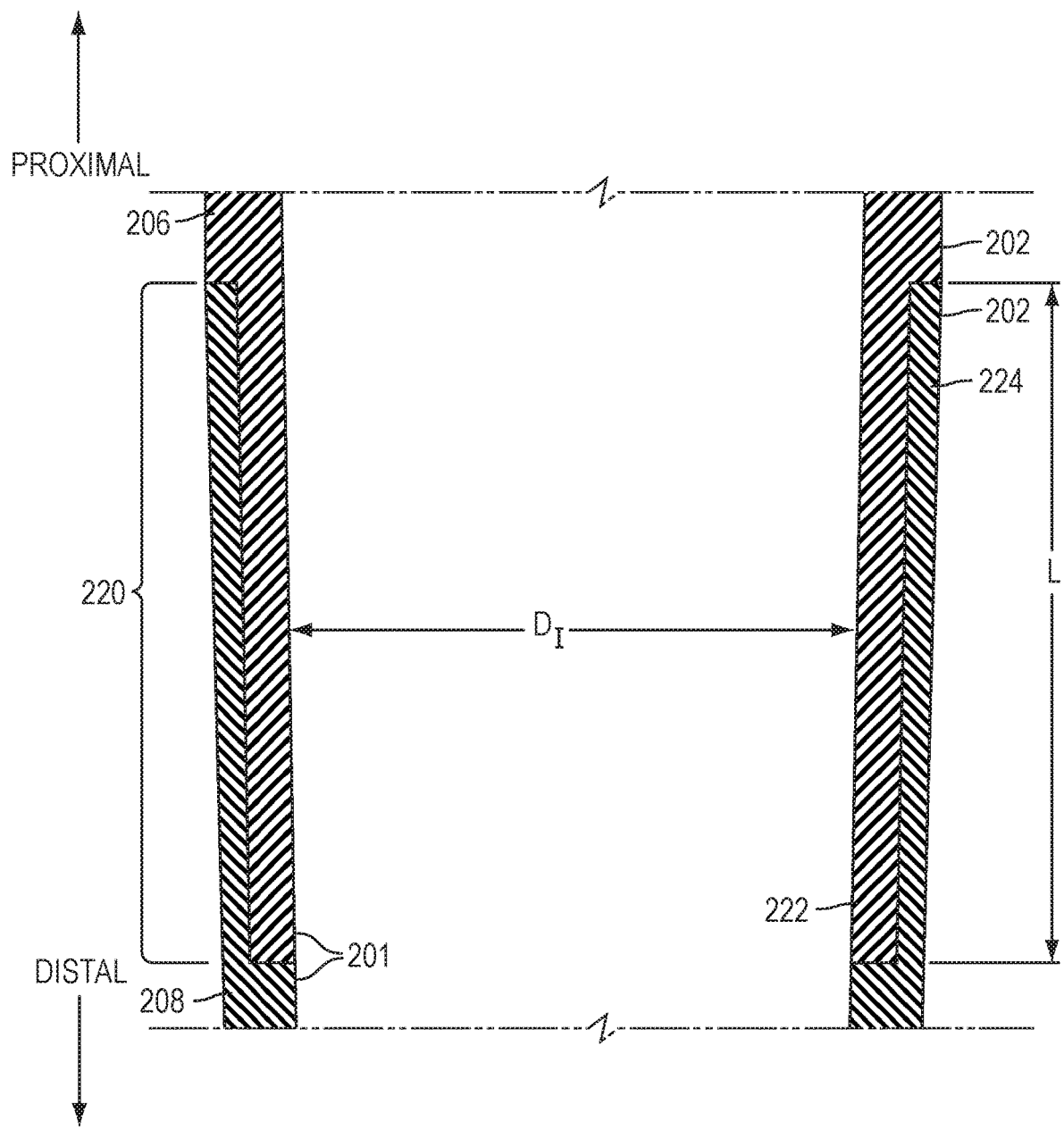
FIG. 2E is a detailed cross-sectional view of the joint of the strengthened portion and transparent portion of the cannula of FIGS. 2A and 2B.

Referring to FIGS. 2B and 2E, the strengthened portion 206 and the transparent portion 208 of the cannula 200 are joined at a joint 220. The joint 220 is a region of the cannula 200 wherein the distal end of the strengthened portion 206 and the proximal end of the transparent portion 208 overlap one another. In the exemplary embodiment of FIGS. 2A-2E, the distal end of the strengthening portion 206 is a male joint part 222 and the proximal end of the transparent portion 208 is a complimentary female joint part 224, although the male and female joint parts may be reversed. Male joint part 222 and complimentary female joint part 224 may be joined by, for example, by welding, overmolding, two-shot molding, or solvent bonding.

Although the joint may be positioned anywhere along the length of the cannula, it may be desirable to position the joint proximally adjacent to the remote center of the cannula so as to maximize the length of the strengthened portion, while still ensuring that the transparent portion of the cannula extends from the remote center to the distal end of the cannula. Providing transparency at this portion of a cannula insertion tube allows a surgeon to check that the remote center of the cannula is properly disposed within a port relative to the patient body wall.

Referring to the exemplary embodiment of FIG. 2E, the cannula insertion tube 205 has have an inner diameter $D_I$ and the joint 220 of the cannula 200 has a length L (i.e., the length of overlap L between the male joint part 222 and the complimentary female joint part 224). The strength at the joint 220 is proportional to the length of overlap L between the male joint part 222 and the complimentary female joint part 224. In various exemplary embodiments the ratio of the joint length L to the cannula insertion tube inner diameter $D_I$ may range from about 1:1 to about 2:1, for example, the ratio may be about 1:1, about 2:1, or for example about 3:2. Where the male joint part 222 and the complimentary female joint part 224 are joined via chemical bond formed during a molding process, a person having ordinary skill in the art would understand that the joint length L should be large enough to provide an area of chemical bonding that is sufficient to withstand expected loads.

Other joint configurations not shown in the figures also are contemplated, such as, for example, end-to-end reversal of male and female joint parts. The selection of the disposition of male and female may be based on purely cosmetic considerations. However, configuring the joint such that the distal end of the strengthened portion has the male joint part and the proximal end of the transparent portion has the female joint part may be a slightly stronger embodiment than the reversed joint part configuration. Alternatively or in addition to chemical bonding, the joint parts can incorporate mechanical interlocking features to achieve or further enhance the axial and/or rotational strength. Mechanical interlocking features may include, for example, protrusions (e.g., ridges, bumps, or the like) and corresponding recesses.

With reference to FIGS. 3A through 3E, another exemplary embodiment of cannula 300 in accordance with the present disclosure is illustrated. Cannula 300 has a cannula insertion tube 305 that has a strengthened portion 306 and a transparent portion 308. A bowl portion 310 is disposed at a proximal end of the cannula 300. As described above with reference to cannula 200, bowl portion 310 can have a funnel-like configuration with the cannula insertion tube 305 extending from a narrowed end of the funnel shaped bowl portion 310. The cannula insertion tube 305 extends distally from the bowl portion 310. The strengthened portion 306 may be made of a reinforced plastic material. For example, the strengthened portion 306 may be made of a plastic material compounded with strengthening fibers, such as, for example, glass, carbon and/or aramid fibers, as described above. The strengthening fibers provide increased strength, but may decrease the transparency of the plastic material alone such that the strengthening portion 306 is relatively opaque. In one exemplary embodiment, the material of the strengthened portion is polycarbonate compounded with about 10% to about 30% fibers. The fibers may be at least one of glass fibers, carbon fibers, aramid fibers, and/or any other suitable fiber material. Alternatively, in an exemplary embodiment, the strengthened portion is made out of metal, such as, for example, stainless steel and/or any other suitable metal.

The transparent portion 308 may be made of a clear material, such as a clear plastic material, as described above. In various exemplary embodiments, the transparent portion is made of polycarbonate and does not include a reinforcing material, such as strengthening fibers. When an endoscopic sensing device (e.g., an endoscopic image capture device) is inserted through a cannula 300, the relative transparency of the transparent portion 308 can provide a wider field of view of the surgical or treatment site as the endoscopic device is retracted at least partially into a distal end of the cannula 300 so that it is disposed within the transparent portion 308.

Cannula insertion tube 305 has an inner lateral wall surface 301 (shown within the transparent portion 308 in FIGS. 3B and 3D, but hidden from view within the opaque strengthened portion 306) and an outer lateral wall surface 302. The inner lateral wall surface 301 may be cylindrical or slightly distally tapered with rounded transverse cross-sections along the length, as described above. Also, the outer lateral wall surface 302 may be cylindrical or slightly distally tapered with rounded transverse cross-sections along the length, as described above. It is also contemplated that the outer lateral wall surface 302 can include two or more tapered portions along the length of its cannula insertion tube 305, as described below.

As with the embodiment of FIGS. 2A-2E, described above, the cannula 300 of the exemplary embodiment of FIGS. 3A-3E also includes indicia that assists placement of the cannula relative to the body wall of a patient in an inserted position of the cannula. For example, central, upper, and lower body wall targets 312, 314, and 316 similar to those described above may be included on the cannula insertion tube 305. Moreover, the remote center 318 of the cannula 300 may be at or near the center of the central body wall target 312. Alternatively, it is also contemplated that the center of the central body wall target of a cannula can be offset from the remote center of the cannula.

In various exemplary embodiments that utilize indicia to assist in placement of the cannula relative to a body wall, such indicia is not limited to the configurations shown and described in the figures, but can take numerous other forms without departing from the scope of the present disclosure. For example, the target indicia may be formed by regions free from peripheral ribs (e.g., ribs 335) and/or colored regions or other markings on an external surface of the cannula. Those having ordinary skill in the art would appreciate numerous ways in which indicia may be provided on the cannula without departing from the scope of the present disclosure.

Figure 3A:
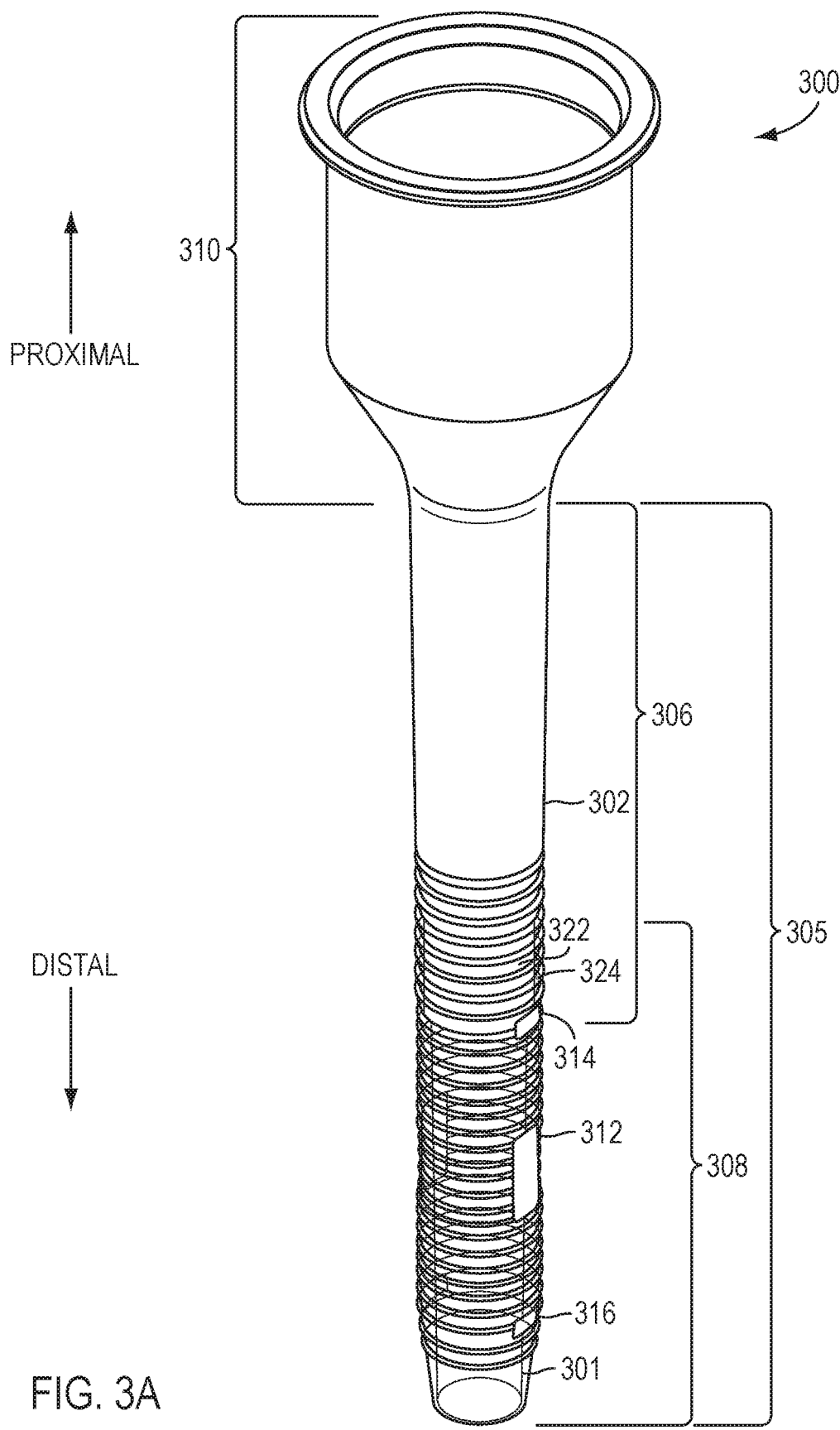
FIG. 3A is a perspective view of another exemplary embodiment of a cannula in accordance with the present disclosure.
Figure 3B:
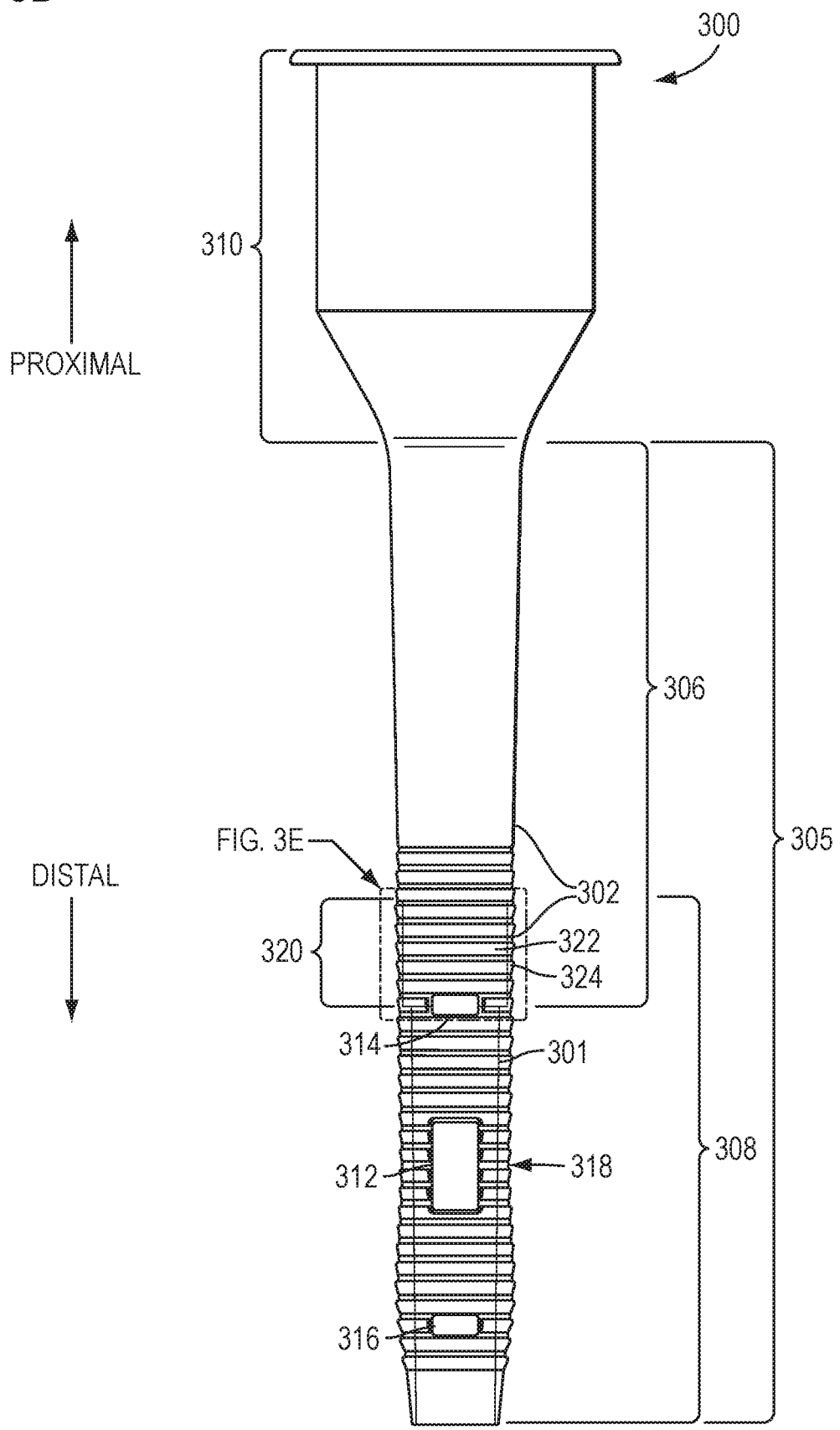
FIG. 3B side view of the cannula of FIG. 3A.
Figure 3C:
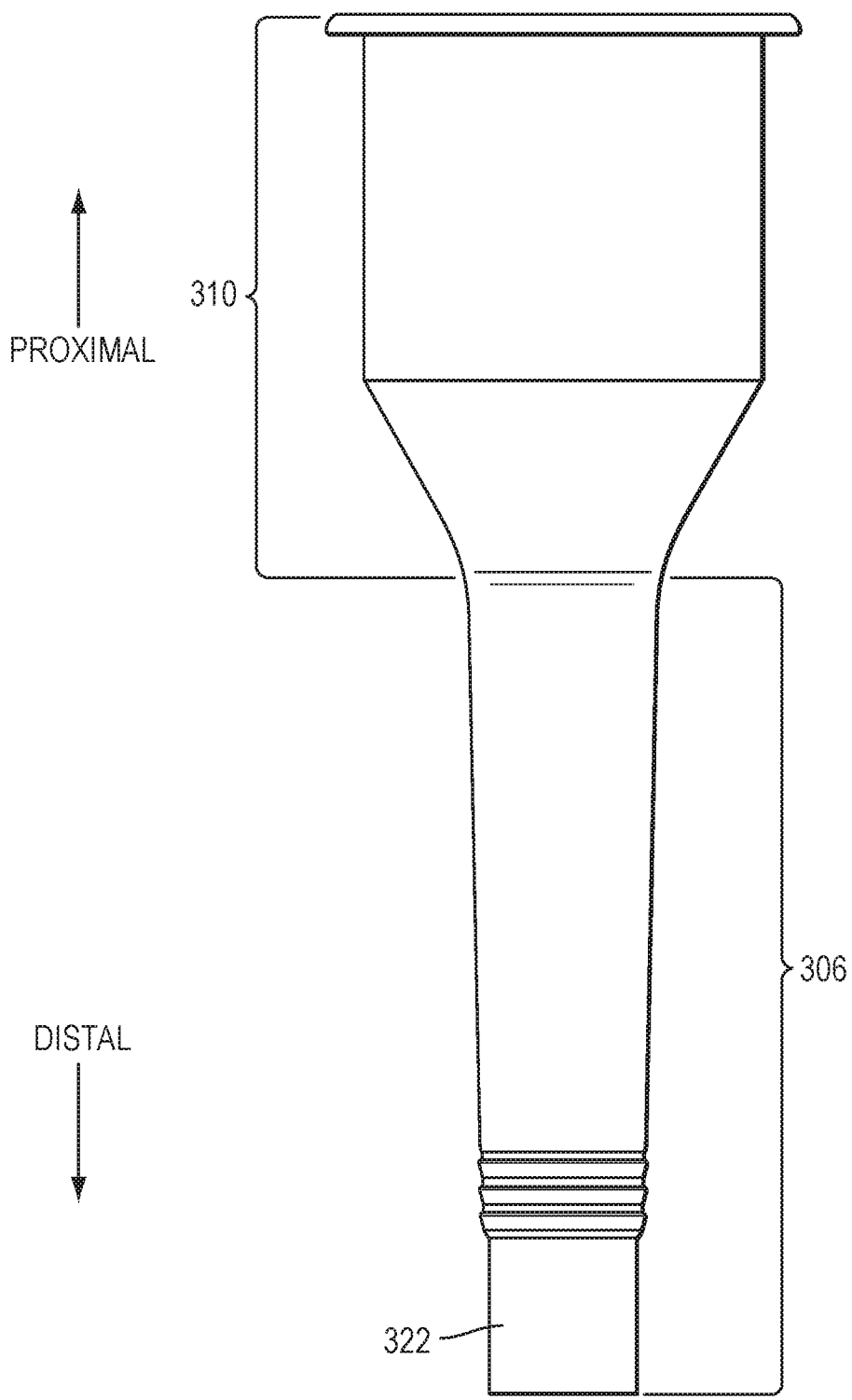
FIG. 3C is a detailed side view of portions of the cannula of FIGS. 3A and 3B.
Figure 3D:
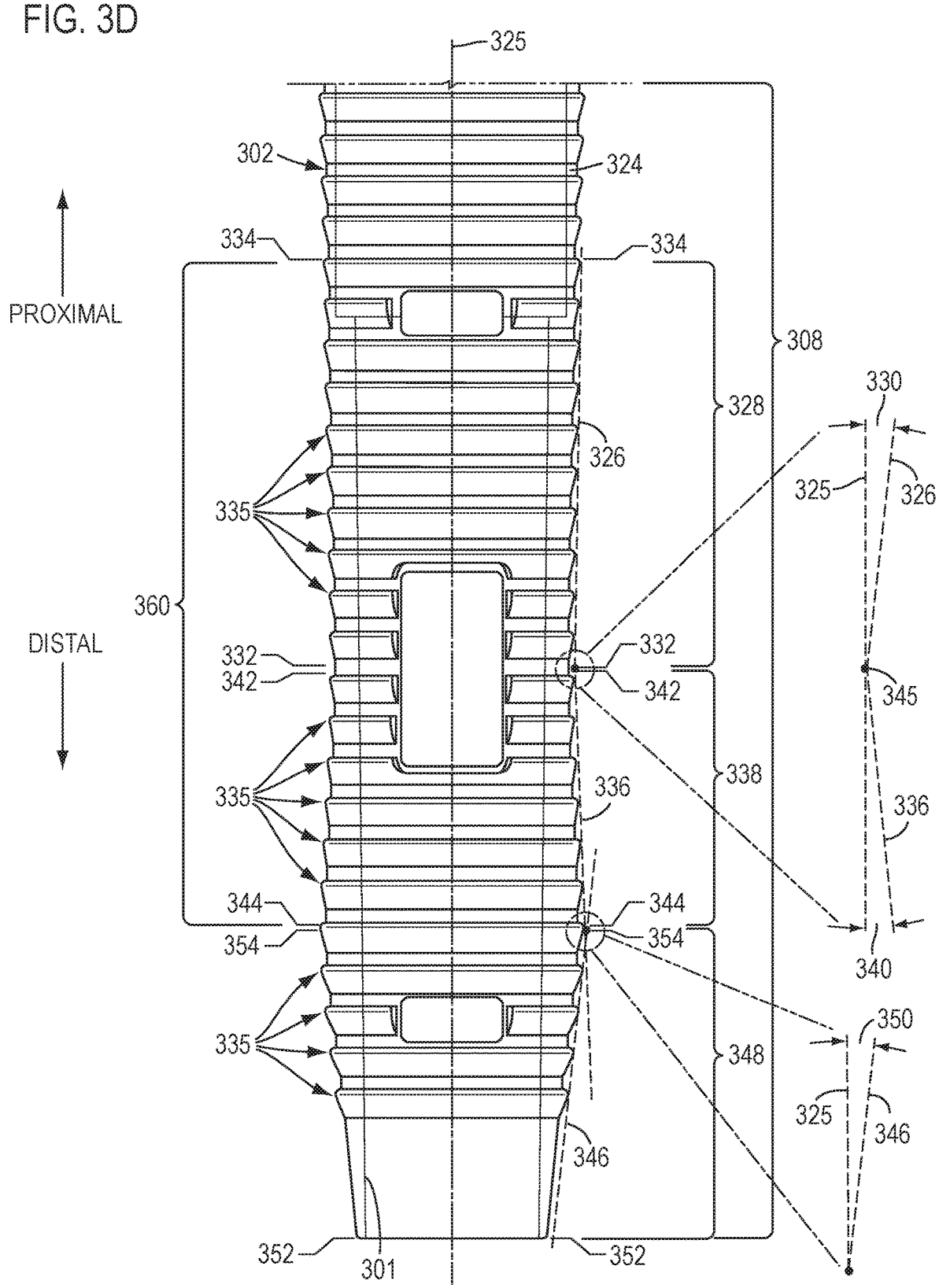
FIG. 3D is a detailed side view of another portion of the cannula of FIGS. 3A and 3B.
Figure 3E:
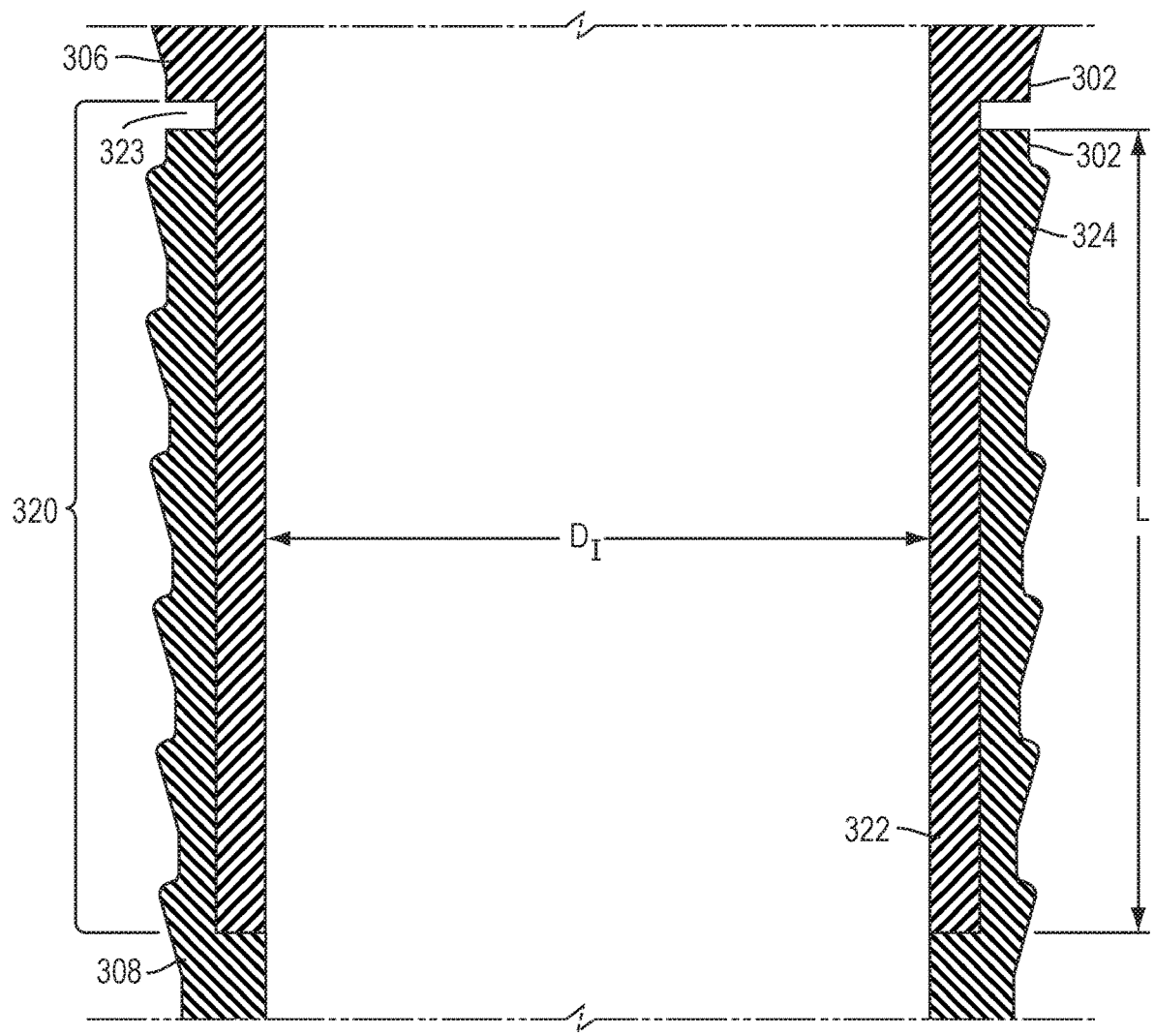
FIG. 3E is a detailed cross-sectional view of the joint of the strengthened portion and transparent portion of the cannula of FIGS. 3A and 3B.

Referring to FIGS. 3B and 3E, the strengthened portion 306 and the transparent portion 308 of the cannula 300 are joined at a joint 320 in a manner like that described with reference to FIGS. 2A-2E above, and thus such description is not repeated here. The joint 320 is defined by the region of the cannula 300 wherein the distal end of the strengthened portion 306 and the proximal end of the transparent portion 308 overlap one another. In the exemplary embodiment of FIGS. 3A-3E, the distal end of the strengthening portion 306 may be a male joint part 322 and the proximal end of the transparent portion 208 may be a complimentary female joint part 324. Male joint part 322 and complimentary female joint part 324 may be joined by, for example, by welding, overmolding, two-shot molding, or solvent bonding. As shown in FIG. 3E, the outer lateral wall surface 302 may have a circumferential gap 323 at the joint 320. The circumferential gap 323 may serve as a reveal that allows for tolerance stack ups in the manufacture of the cannula 300 via welding and adhesion. In an overmold or two shot manufacturing approach, the gap 323 may be eliminated.

Referring again to FIG. 3E, the cannula insertion tube 305 may have an inner diameter $D_I$ and the joint 320 of the cannula 300 may have a length L (i.e., the length of overlap L between the male joint part 322 and the complimentary female joint part 324). The strength of the joint 320 may be proportional to the length of overlap L between the male joint part 322 and the complimentary female joint part 324. As with the exemplary embodiment of FIGS. 2A-2E, the ratio of the joint length L to the cannula insertion tube inner diameter $D_I$ may range from about 1:1 to about 2:1; for example, the ratio may be about 1:1, about 2:1, or for example about 3:2. In addition, the male and female joint parts may be reversed, as described above.

As shown in FIG. 3D, to further enhance stiffness and strength, cannula 300 includes a variation in the cannula tube wall thickness obtained by varying the outer lateral dimensions (e.g., diameter) along a length (e.g., axial direction) of the cannula insertion tube 305 while maintaining a uniformly sized cross-section or slightly distally tapered inner lateral wall surface 301 along the length, as described above. For example, a cannula may include a tapered outer surface region relative to other portions along a length of the cannula insertion tube. Such a tapered region may be configured such that the portion(s) of the tapered region with the greatest outer dimension (i.e., greatest lateral wall thickness) are located at one or more portions along the length of the cannula that tend to be subject to relatively higher bending moments, and the portion(s) of the tapered region with the smallest outer dimensions (i.e., smallest lateral wall thickness) are located at a portion along the length of the cannula where a body wall of a patient is intended to sit when the cannula is in an inserted position, thereby simultaneously increasing the strength of the cannula and minimizing the lateral dimensions of the cannula so as to not require a larger size port, opening, and/or incision within the body wall of a patient.

A tapered region also can provide increased retention forces by inhibiting the body wall from moving past an increasing lateral dimension of the tapered region in response to a force tending to move the cannula in the axial direction relative to the body wall. Although a tapered region may be provided in various locations along the cannula, in one exemplary embodiment a tapered region may be located at a region of the cannula proximal to a region along a length of the cannula intended to be in contact with the body wall in the inserted position. A tapered region could alternatively, or in addition to, be provided proximal to the body wall contact region of the cannula.

As best shown in FIG. 3D, two tapered regions, first tapered portion 328 and second tapered portion 338, can be provided to form a waisted portion 360 along a cannula insertion tube 305. At least one region having larger outer lateral dimensions than the waisted portion can extend proximally or distally from the waisted portion. For example, in cannula insertion tube 305, a region that encompasses a proximal end of the transparent portion 308 as well as the strengthened portion 306 extends proximally from the waisted portion 360.

More specifically, in the exemplary embodiment of FIGS. 3A-3E, cannula insertion tube 305 has lateral outer dimensions that include a first taper 326 that defines the lateral (e.g., radial) outer limits of a first tapered portion 328 of a cannula 300. The first taper 326 has a first taper angle 330 that can be measured relative to a longitudinal axis 325 of the cannula 300. First tapered portion 328 has a first tapered portion narrow end 332 and a first tapered portion wide end 334.

Various first taper angle 330 sizes are contemplated. For example, the size of the first taper angle 330 may range from about 1° to about 5°. The longitudinal length of the first tapered region 328 (i.e., the length of the first tapered region extending from the first tapered portion narrow end 332 and a first tapered portion wide end 334) may be considered when sizing the first taper angle 330. For example, when the longitudinal length of the first tapered region 328 is relatively large (e.g., about 50 to about 100 millimeters in length), the size of the first taper angle 330 may range from about 1° to about 2°. Alternatively, for example, when the longitudinal length of the first tapered region 328 is relatively small (e.g., about 20 to about 50 millimeters in length), the size of the first taper angle 330 may range from about 2° to about 3°. In some embodiments, the size of the first taper angle 330 is about 1°.

Additionally, the lateral outer dimensions of cannula insertion tube 305 include a second taper 336 that defines the lateral (e.g., radial) outer limits of a second tapered portion 338 of the cannula 300. The second taper 336 of a cannula 300 has a second taper angle 340 that can be measured relative to a longitudinal axis 325 of the cannula 300. Second tapered portion 338 has a second tapered portion narrow end 342 and a second tapered portion wide end 344.

Various second taper angle 340 sizes are contemplated. For example, the size of the second taper angle 340 may range from about −1° to about −5°. The longitudinal length of the second tapered portion 338 (i.e., the length of the second tapered region extending from the second tapered portion narrow end 342 to the second tapered portion wide end 344) may be considered when sizing the second taper angle 340. For example, when the longitudinal length of the second tapered portion 338 is relatively large (e.g., about 20 to about 40 millimeters in length), the size of the second taper angle 340 may range from about −1° to about −2°. Alternatively, for example, when the longitudinal length of the second tapered portion 338 is relatively small (e.g., about 5 to 20 millimeters in length), the size of the second taper angle 340 may range from about −2° to about −3°. In some embodiments, the size of the second taper angle 340 is about −1°.

The narrow end 332 of the first tapered portion 328 can be slightly axially spaced from the narrow end 342 of the second tapered portion 338, although it is also contemplated that they could be at approximately the same axial position. The second tapered portion 338 and the first tapered portion 328 may be integral or distinct components. The meeting location of the narrow ends 332 and 342 define an inflection 345 (also "inflection location 345") of the waisted portion 360 of the cannula 300. In an exemplary embodiment, the remote center 318 of the cannula 300 can be disposed at the inflection 345. The cannula 300 can be inserted within a patient such that the body wall is disposed to surround the inflection location 345 of the cannula 300.

As further depicted in FIG. 3D, the outer lateral dimensions of cannula insertion tube 305 also optionally includes a third taper 346 that defines the lateral (e.g., radial) outer limits of a third tapered portion 348. The third tapered portion 348 includes a distal end of the cannula 300, with proximal and distal directions labeled on FIG. 3D. The third taper 346 has a third taper angle 350 that can be measured relative to a longitudinal axis 325 of the cannula 300. Third tapered portion 348 has a third tapered portion narrow end 352 and a third tapered portion wide end 354.

Various third taper angle 350 sizes are contemplated. For example, the size of the third taper angle 350 may range from about 1° to about 5°. The longitudinal length of the third tapered portion 348 (i.e., the length of the third tapered portion 348 extending from the third tapered portion narrow end 352 and a third tapered portion wide end 354) may be considered when sizing the third taper angle 350. For example, when the longitudinal length of the third tapered portion 348 is relatively large (e.g., about 20 to 50 millimeters in length), the size of the third taper angle 350 may range from about 1° to about 2°. Alternatively, for example, when the longitudinal length of the third tapered portion 348 is relatively small (e.g., about 5 to about 20 millimeters in length), the size of the third taper angle 350 may range from about 2° to about 3°. In some embodiments, the size of the third taper angle 350 is about 2°.

In various embodiments, the magnitude of the size of the first taper angle 330 and the magnitude the size of the second taper angle 340 may be about the same. Further, in some embodiments, the magnitude of the size of the third taper angle 350 may be relatively larger than the magnitude of the size of the first taper angle 330 and/or the magnitude the size of the second taper angle 340. Thus, in various exemplary embodiments, the size of the first taper angle 330 is from about 1° to about 2°, the size of the second taper angle 340 is from about −1° to about −2°, and the size of the third taper angle 350 is from about 2° to about 3°. Accordingly, in an exemplary embodiment, the size of the first taper angle 330 is about 1°, the size of the second taper angle 340 is about −1°, and the size of the third taper angle 350 is about 2°.

The wide end 344 of the second tapered portion 338 may be collocated or slightly axially spaced from the wide end 354 of the third tapered portion 348. The second tapered portion 338 and the third tapered portion 348 of cannula 300 may be integral or distinct components.

In an alternative embodiment, it is envisioned as within the scope of the present disclosure that instead of having the third taper 346, the cannula 300 can have outer lateral dimensions such that the cannula outer surface extends straight from wide end 344 of the second tapered portion 338 to the distal end of the cannula 300 (i.e., the size of the taper angle 3500 may be about 0°).

Additional details regarding contemplated waisted portion and/or tapered portion(s) configurations are disclosed in U.S. patent application Ser. No. 15/622,935, filed on Jun. 14, 2017, which claims priority to U.S. Provisional Patent Application No. 62/365,778, filed on Jul. 22, 2017, titled "CANNULAS HAVING BODY WALL RETENTION FEATURES, AND RELATED SYSTEMS AND METHODS," which is hereby incorporated by reference herein in its entirety.

Rather than a smooth outer wall surface, a portion or all of the cannula insertion tube 305 can include ribs. For example, as best shown in FIGS. 3C and 3D, part of the strengthened portion 306 and the transparent portion 308 have ribs 335 that laterally extend from the outer lateral wall surface 302. In various exemplary embodiments, as best shown in FIG. 3C, ribs 335 only extend on a part of the strengthened portion 306 and a distal portion thereof is left free of ribs so as to achieve a smooth male joint part 322 that is able to mate a female joint part 324 so as to form joint 320. Ribs 335 may provide increased retention forces by inhibiting the cannula 300 in an inserted position from sliding axially relative to the body wall in response to a force tending to push or pull the cannula in an axial direction relative to the body wall. In various exemplary embodiments, the dimensions of the ribs may be configured to provide tapered outer surface profiles to the cannula, as discussed above.

In FIGS. 3B and 3D, the ribs 335 are uniformly spaced apart in the axial direction. Alternatively, the ribs 335 of a cannula in accordance with the present disclosure can be non-uniformly spaced, i.e. the space between the each adjacent pair of ribs can be varied with respect to the space between one or more other pair of adjacent ribs. The total number of ribs 335 on the cannula 300 can be varied. Also, the number of ribs 335 within each tapered portion 328, 338, and 348 may be varied. Along a longitudinal cross-sectional plane of the cannula 300, the outer lateral wall surface 302 may be parallel to each taper 326, 336, and 346, i.e., the orientation of outer lateral wall surface 302 along a longitudinal cross-sectional plane of the cannula 300 within tapered portions 328, 338, and 348 is parallel to that of the tapers 326, 336, and 346, respectively.

Figure 4A:
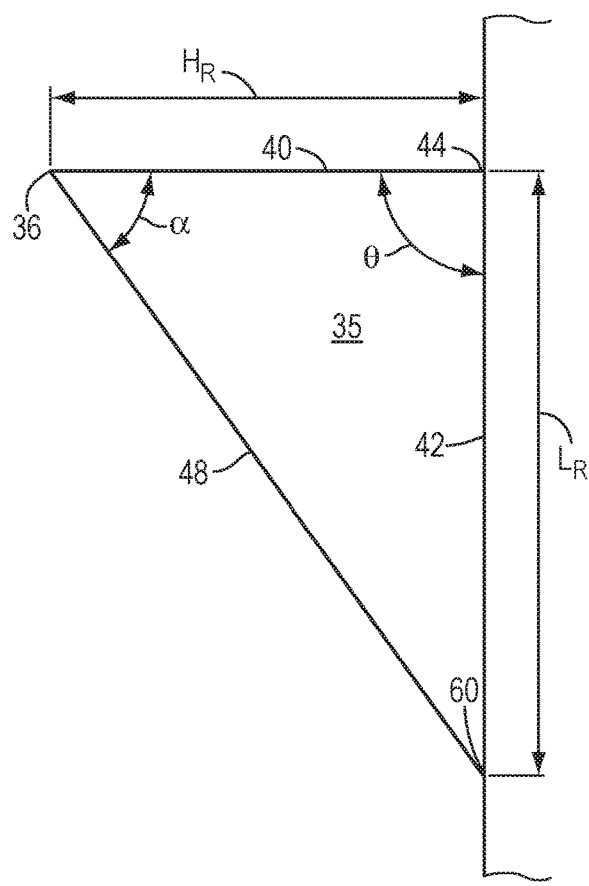
FIG. 4A is a partial longitudinal cross sectional view of an exemplary embodiment of a rib of a cannula according to the present disclosure.
Figure 4B:
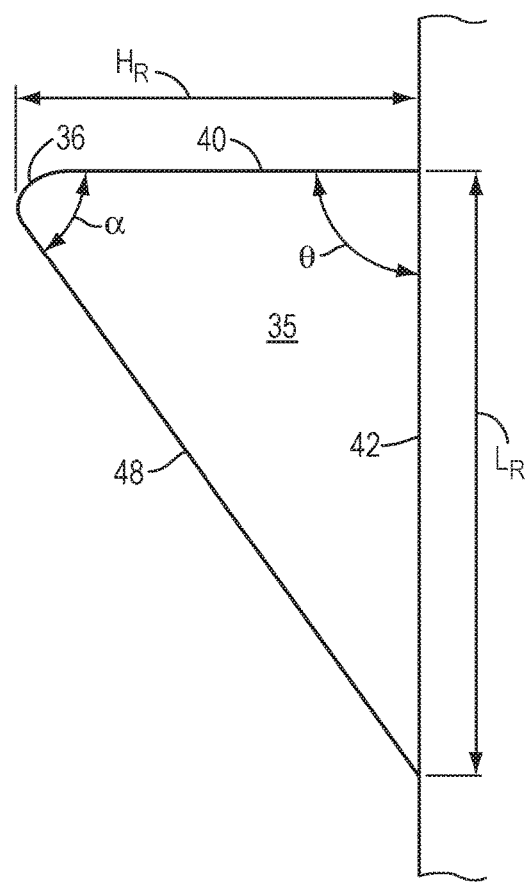
FIG. 4B is a partial longitudinal cross sectional view of another exemplary embodiment of a rib of a cannula according to the present disclosure.
Figure 4C:
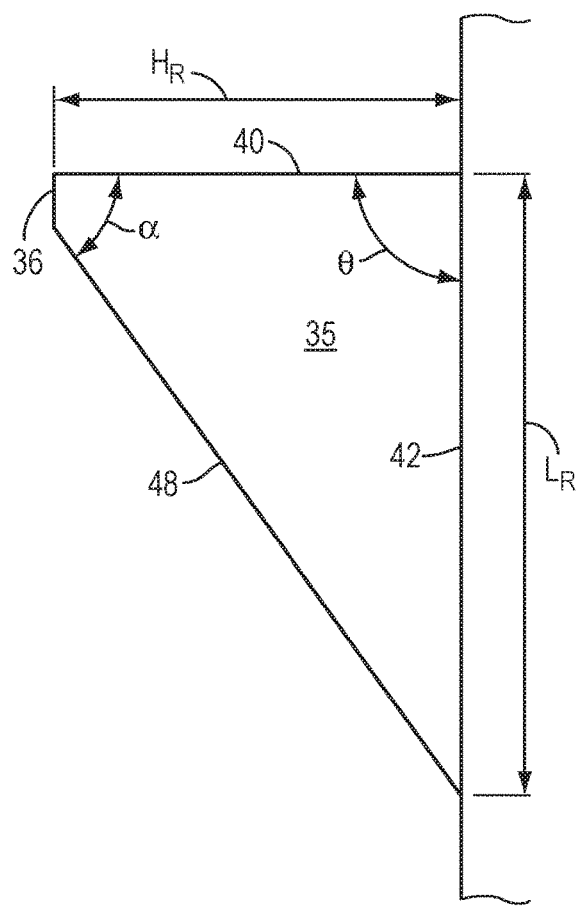
FIG. 4C is a partial longitudinal cross sectional view of another exemplary embodiment of a rib of a cannula according to the present disclosure.
Figure 4D:
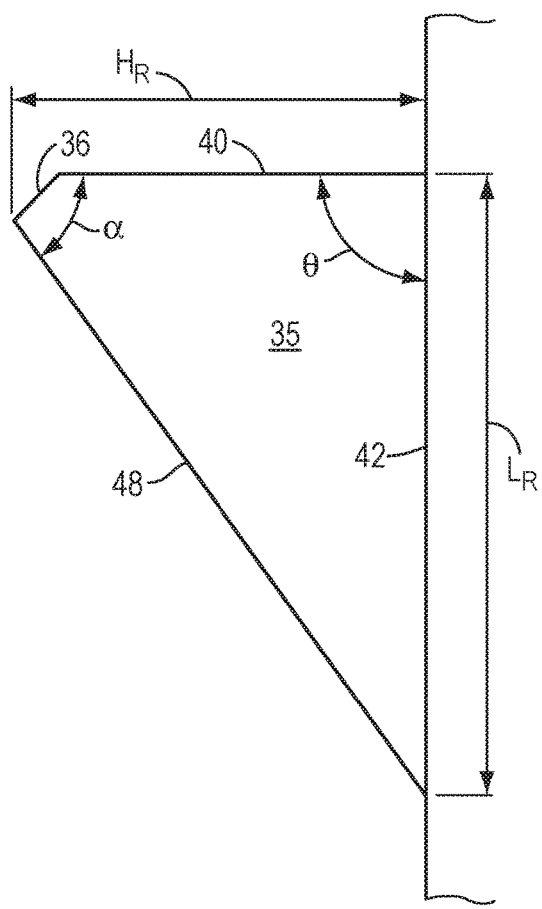
FIG. 4D is a partial longitudinal cross sectional view of yet another exemplary embodiment of a rib of a cannula according to the present disclosure.

With reference to FIG. 4A, a longitudinal cross-sectional view through one rib showing the profile of the rib relative to the outer wall of the cannula is schematically represented to illustrate various design parameters of ribs, such as ribs 335 and ribs to be described further below. Each rib 35 of FIG. 4A has a height $H_R$, a length $L_R$, and an apex 36 defining an apex angle α. As exemplified by cannula 300 (see FIG. 3D), the height $H_R$, length $L_R$, and apex angle α of each rib 35 can be the same as the height $H_R$, length $L_R$, and apex angle α of every other rib 35. Alternatively, in another exemplary embodiment in accordance with the present disclosure, the height $H_R$, length $L_R$, and/or apex angle α of each rib 35 may be varied with respect to the height $H_R$, length $L_R$, and/or apex angle α of one or more of the other ribs 35. Although the exemplary FIGS. 4A-4D show apex angle α as approximately 55 degrees, it is contemplated that the apex angle of a rib may range from about 35 degrees to about 75 degrees. The apex 36 may be pointed, as shown in FIG. 4A. Alternatively, the apex 36 may be rounded (see FIG. 4B), flattened (see FIG. 4C), or flattened and angled (see FIG. 4D).

As shown in FIG. 4A, the height $H_R$ of each rib 35 is the radial distance of each radial rib wall 40, with the rib wall 40 being the surface extending radially outward relative to the cannula longitudinal axis. The length $L_R$ of each rib 35 is the rib base 42, with the rib base 42 being the portion of the rib extending axially along the cannula from the end 44 of the radial rib wall 40. The radial rib wall 40 forms an angle θ with the rib base 42. Although FIGS. 4A-4D show angle θ as an approximate right angle, it is contemplated that the angle θ of a rib may be greater than or less than 90 degrees, for example, angle θ may range from about 70 degrees to about 110 degrees. A rib lateral wall 48 extends from the apex 36 to a second end 60 of the rib base 42. Each rib 35 may be integral with or distinct from the outer lateral wall surface (e.g., 302 of FIGS. 3A-3E) of the cannula.

The rib configurations shown in FIGS. 3A-3E and 4A-4D are to be taken as non-limiting examples of the possible rib configurations and geometry for a ribbed cannula in accordance with the present disclosure. For example, although FIGS. 3A-3E and 4A-4D are discussed as displaying exemplary longitudinal cross sectional geometry of longitudinally spaced, annular ribs (i.e., ring-shaped ribs), ribs of a cannula according to the present disclosure may alternatively take the form of helical threads. Moreover, alternative longitudinal cross sectional geometry of a rib of a cannula according to the present disclosure in addition to those shown in FIGS. 4A-4D is also contemplated. For example, although not shown, in various exemplary embodiments according to the present disclosure, ribs of a cannula may have a sine-like, triangle, saw tooth, and/or rectangle waveform cross section. Additional details regarding contemplated rib configurations are disclosed in the U.S. patent application Ser. No. 15/622,935, filed on Jul. 14, 2017, which claims priority to U.S. Provisional Patent Application No. 62/365,778, filed on Jun. 22, 2017, titled "CANNULAS HAVING BODY WALL RETENTION FEATURES, AND RELATED SYSTEMS AND METHODS," which is hereby incorporated by reference herein in its entirety.

Referring again to FIG. 3D, the apex of each rib 335 of the first tapered portion 328 may be incident upon an imaginary surface (shown in dotted line) that defines the first taper 326. Likewise, the apex of each rib 335 of the second tapered portion 338 may be incident upon an imaginary surface (shown in dotted line) that defines the second taper 336 and, the apex of each rib 335 of the third tapered portion 348 may be incident upon imaginary surface (shown in dotted line) that defines the third taper 346. The tapers 326, 336, and 346 are achieved by varying the thickness of the cannula wall, i.e., by varying the lateral distance between the outer lateral wall surface and the inner lateral wall surface. The tapered portions 328, 338, and 348 are configured such that the wide ends 334, 344, and 354 of the tapered portions 328, 338, and 348, which have the largest lateral wall thickness, are located at portions along the length of the cannula that tend to be subject to relatively higher bending moments, and the narrow ends 332, 342 of the tapered portions 328, 338 which have the smallest lateral wall thickness are located at a portions along the length of the cannula where a body wall of a patient is intended to sit when the cannula is in an inserted position, thereby simultaneously increasing the strength of the cannula and minimizing the lateral dimensions of the cannula so as to not require a larger size port, opening, and/or incision within the body wall of a patient.

Although FIGS. 3A-3E depict a cannula with three tapered portions 328, 338, and 348 that are disposed adjacent and in series along a length of the cannula insertion tube 305, other configurations are contemplated. A cannula insertion tube may include one, two, three, or more tapered portions, and the portions may be arranged adjacent to one another or spaced apart by non-tapered (e.g., cylindrical) portion. Further, the disposition of the one or more tapered portions may be varied along the length of the cannula insertion tube, such as, for example, a strengthened portion of the cannula insertion tube may include one or more of the tapered portions. Additionally, while it is contemplated that a cannula with a cannula insertion tube having a smooth outer wall surface, such as, for example cannula 200 of FIGS. 2A-2E, could include one or more tapered portions along the length of its cannula insertion tube 205, cannulas in accordance with the present disclosure may have insertion tubes that do not include tapered portions.

Although FIGS. 3A-3E depict a cannula with ribs 335 along a part of the strengthened portion 306 of the cannula insertion tube 305 and a part of the transparent portion 308 of the cannula insertion tube 305, other rib configurations are also contemplated. For example, it is contemplated that ribs may be disposed along the entire length of the cannula insertion tube 305. It is also contemplated that the ribs may be exclusively disposed on just one of either the strengthened portion or the transparent portion, such as, for example, an cannula insertion tube with a smooth strengthened portion and a wholly or partially ribbed transparent portion is contemplated, or vice versa.

In addition, although various exemplary embodiments describe the strengthened portion being made of a reinforced plastic material, the present disclosure contemplates a strengthened portion that is made of other materials, such as metals, for example, stainless steel. A metal strengthened portion may be joined to a transparent portion via a chemical bond as a result of an overmolding process and/or mechanical interlocking features as set forth above.

The cannulas in accordance with various exemplary embodiments of the present disclosure have various applications, such as in various minimally invasive surgical procedures. Contemplated surgical procedures include diagnostic surgical procedures and therapeutic surgical procedures.

Although the cannulas have been described herein with reference to teleoperated, computer-assisted surgical systems, the present disclosure contemplates non-teleoperated surgical instruments, such as, for example, manually operated surgical instruments (e.g., hand held surgical instruments), which may be used with the various exemplary embodiments described herein.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the scope of the present disclosure and following claims.

The nature of information depicted in the figures and described herein is exemplary. Those persons having skilled in the art would appreciate modifications to the cannulas can be made, such as for example, modifications to structure, dimensions, materials, and methodologies may be made without departing from the scope of the present disclosure.

It is to be understood that the particular examples and embodiments set forth herein are non-limiting, and modifications to structure, dimensions, materials, and methodologies may be made without departing from the scope of the present disclosure and claims including equivalents.

Other embodiments in accordance with the present disclosure will be apparent to those skilled in the art from consideration of the specification and practice of the invention disclosed herein. It is intended that the specification and examples be considered as exemplary only, with being entitled to their full breadth of scope, including equivalents.

What is claimed is:

1. A cannula comprising:
  a bowl portion comprising a proximal first opening and a distal second opening, the first opening being larger than the second opening; and
  an insertion tube comprising:
    a distal end to which the insertion tube extends from the bowl portion, a predefined remote center of motion location of the cannula to which the cannula is inserted into a patient to perform a medical procedure, a proximal strengthened portion located proximally of the remote center of motion location, a distal transparent portion extending proximally from the distal end of the insertion tube through the remote center of motion location and having a higher transparency compared to the strengthened portion, and a passage extending from the second opening of the bowl portion through the strengthened portion and the transparent portion and terminating in an opening at the distal end of the insertion tube.

2. The cannula of claim 1, wherein the strengthened portion extends from the bowl portion to the remote center of motion location.

3. The cannula of claim 1, wherein the transparent portion comprises a clear plastic.

4. The cannula of claim 3, wherein the clear plastic comprises a material selected from the group consisting of: polycarbonate, acrylic, and polysulfone.

5. The cannula of claim 1 further comprising one or more ribs on an outer surface of the insertion tube.

6. The cannula of claim 5, wherein the one or more ribs extend around the outer surface of the insertion tube.

7. The cannula of claim 1, wherein the strengthened portion and the transparent portion partially overlap each other to form a joint along a length of the insertion tube.

8. The cannula of claim 7, wherein the strengthened portion and the transparent portion are welded, overmolded, two-shot molded, or solvent bonded together at the joint.

9. The cannula of claim 7, wherein a ratio of a longitudinal length of the joint to a diameter of the passage at the joint ranges from 1:1 to 2:1.

10. The cannula of claim 1, wherein the strengthened portion comprises a reinforced plastic material.

11. The cannula of claim 10, wherein the reinforced plastic material comprises a material selected from the group of plastics consisting of polycarbonate, ABS, polycarbonate-ABS, polypropylene, nylon, and polyphenysulfone.

12. The cannula of claim 10, wherein the strengthened portion is a plastic compounded with 10 percent to 30 percent fiber.

13. The cannula of claim 12, wherein the fiber comprises a material selected from the group of fibers consisting of glass fiber, carbon fiber, and aramid fiber.

14. The cannula of claim 12, wherein the distal transparent portion is made of a material free of fibers.

15. The cannula of claim 1, wherein the insertion tube comprises a waisted portion and a non-waisted portion, the waisted portion having an outer diameter smaller than the non-waisted portion.

16. The cannula of claim 15, wherein:

the transparent portion comprises the waisted portion with a non-uniform lateral thickness between an inner surface and an outer surface of the insertion tube; and the strengthened portion comprises one region with an outer diameter larger than an outer diameter of the waisted portion and with a uniform or distally tapered lateral thickness between the inner surface and the outer surface of the insertion tube.

17. The cannula of claim 15, wherein the waisted portion comprises:

a first tapered portion including a first tapered portion narrow end and first tapered portion wide end, wherein the first tapered portion is at least partially incident upon a first imaginary surface defining a first taper;

a second tapered portion including a second tapered portion narrow end and second tapered portion wide end, wherein the second tapered portion is at least partially incident upon a second imaginary surface defining a second taper; and a meeting location of the first tapered portion narrow end and the second tapered portion narrow end, the meeting location defining an inflection of the waisted portion.

18. The cannula of claim 17, wherein, along the length of the insertion tube within the waisted portion, an outer surface of the insertion tube is parallel to the first imaginary surface defining the first taper and the second imaginary surface defining the second taper such that the insertion tube has a non-uniform lateral thickness between an inner surface and the outer surface of the insertion tube.

19. The cannula of claim 17, wherein the remote center of motion location is at the inflection of the waisted portion.

20. The cannula of claim 17, wherein the remote center of motion location is offset from the inflection of the waisted portion.

* * * * *